US010765560B2

(12) United States Patent
Clopp et al.

(10) Patent No.: US 10,765,560 B2
(45) Date of Patent: Sep. 8, 2020

(54) TYMPANOSTOMY TUBE DELIVERY DEVICE WITH ELASTOMERIC BRAKE

(71) Applicant: Tusker Medical, Inc., Menlo Park, CA (US)

(72) Inventors: Mathew D. Clopp, Santa Clara, CA (US); Nga K. Van, San Jose, CA (US)

(73) Assignee: TUSKER MEDICAL, INC., Menlo Park, CA (US)

( * ) Notice: Subject to any disclaimer, the term of this patent is extended or adjusted under 35 U.S.C. 154(b) by 108 days.

(21) Appl. No.: 16/022,041

(22) Filed: Jun. 28, 2018

(65) Prior Publication Data
US 2018/0303673 A1    Oct. 25, 2018

Related U.S. Application Data

(62) Division of application No. 14/455,465, filed on Aug. 8, 2014, now abandoned.

(51) Int. Cl.
*A61F 11/00* (2006.01)
*A61B 17/34* (2006.01)

(52) U.S. Cl.
CPC ........ *A61F 11/002* (2013.01); *A61B 17/3468* (2013.01)

(58) Field of Classification Search
CPC ........ A61F 2/2427; A61F 2/2436; A61F 2/95; A61F 2/9517; A61F 2/962; A61F 2/966;
(Continued)

(56) References Cited

U.S. PATENT DOCUMENTS

| 858,673 A | 7/1907 | Roswell |
| 1,920,006 A | 7/1933 | Dozier et al. |

(Continued)

FOREIGN PATENT DOCUMENTS

| CN | 86105171 A | 3/1987 |
| DE | 19618585 | 11/1997 |

(Continued)

OTHER PUBLICATIONS

Patent Examination Report No. 1 for Australian Patent Application No. 2013209354, dated Oct. 13, 2014, 5 pages.
(Continued)

*Primary Examiner* — Wade Miles
*Assistant Examiner* — Mohammed S Adam

(57) ABSTRACT

An instrument comprises a handpiece, a boss member, a cylindraceous cam body, a linearly movable member, a cam follower, and a braking member. The cam body is rotatably supported in the handpiece and includes an exterior cam feature. The cam follower couples the linearly movable member with the cam feature of the cam body. The cam feature and the cam follower cooperatively drive the linearly movable member linearly in response to rotation of the cam body within the handpiece. The braking member extends about at least a portion of the exterior of the cam body and is positioned to progressively engage the boss member as the cam body rotates within the handpiece. The braking member and the boss member thus cooperate to provide gradual braking of the cam body. The instrument is operable to deploy a pressure equalization tube in the tympanic membrane of a patient.

18 Claims, 25 Drawing Sheets

(58) Field of Classification Search
CPC ........ A61F 2002/9665; A61F 2002/011; A61F 11/002; A61F 11/004; A61F 2/2466; A61F 2/82; A61F 2/0022; A61M 25/0136; A61B 2017/00787; A61B 17/32002; A61B 17/320758; A61B 17/320783; A61B 10/0233
See application file for complete search history.

(56) References Cited

U.S. PATENT DOCUMENTS

| | | |
|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A * | 6/1975 | Akiyama .............. A61F 11/002 606/109 |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A | 6/1988 | Kaufman et al. |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,158,540 A | 10/1992 | Wijay |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A | 3/2000 | Savage et al. |
| 6,045,528 A * | 4/2000 | Arenberg .............. A61F 11/002 604/28 |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,248,112 B1 | 6/2001 | Gambale et al. |
| 6,251,121 B1 | 6/2001 | Saadat |
| 6,258,067 B1 | 7/2001 | Hill |
| D450,843 S | 11/2001 | McGuckin, Jr. et al. |
| 6,319,199 B1 | 11/2001 | Sheehan et al. |
| 6,358,231 B1 | 3/2002 | Schindler et al. |
| 6,398,758 B1 | 6/2002 | Jacobsen et al. |
| 6,416,512 B1 | 7/2002 | Ellman et al. |
| 6,440,102 B1 | 8/2002 | Arenberg et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,626,923 B1 * | 9/2003 | Wyzgala .......... A61B 17/32075 606/159 |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 * | 4/2013 | Lee ...................... A61B 17/062 600/114 |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,320,652 B2 | 4/2016 | Andreas et al. |
| 9,387,124 B2 | 7/2016 | Clifford |
| 9,539,146 B2 | 1/2017 | Girotra et al. |
| 9,681,891 B2 | 6/2017 | Andreas et al. |
| 9,707,131 B2 | 7/2017 | Shahoian |

(56) References Cited

U.S. PATENT DOCUMENTS

| | | | |
|---|---|---|---|
| 9,770,366 B2 | 9/2017 | Liu et al. | |
| 9,833,359 B2 | 12/2017 | Clopp | |
| 9,833,360 B2 | 12/2017 | Andreas et al. | |
| 9,833,601 B2 | 12/2017 | Clifford | |
| 10,517,608 B2* | 12/2019 | Jenkins | A61B 17/24 |
| 2001/0020173 A1 | 9/2001 | Klumb et al. | |
| 2002/0026125 A1 | 2/2002 | Leysieffer | |
| 2002/0069883 A1 | 6/2002 | Hirchenbain | |
| 2002/0111585 A1 | 8/2002 | Lafontaine | |
| 2002/0138091 A1 | 9/2002 | Pflueger | |
| 2002/0161379 A1 | 10/2002 | Kaplan et al. | |
| 2002/0169456 A1 | 11/2002 | Tu et al. | |
| 2003/0018291 A1 | 1/2003 | Hill et al. | |
| 2003/0040717 A1 | 2/2003 | Saulenas et al. | |
| 2003/0060799 A1 | 3/2003 | Arenberg et al. | |
| 2003/0187456 A1 | 10/2003 | Perry | |
| 2003/0199791 A1 | 10/2003 | Boecker et al. | |
| 2004/0054339 A1 | 3/2004 | Clok et al. | |
| 2004/0064024 A1 | 4/2004 | Sommer | |
| 2005/0033343 A1 | 2/2005 | Chermoni | |
| 2005/0165368 A1 | 7/2005 | Py et al. | |
| 2005/0182385 A1 | 8/2005 | Epley | |
| 2005/0187546 A1 | 8/2005 | Bek et al. | |
| 2005/0235422 A1 | 10/2005 | Wallace | |
| 2005/0240147 A1 | 10/2005 | Makower et al. | |
| 2006/0004323 A1 | 1/2006 | Chang et al. | |
| 2006/0095050 A1 | 5/2006 | Hartley et al. | |
| 2006/0142700 A1 | 6/2006 | Sobelman et al. | |
| 2006/0155304 A1 | 7/2006 | Kaplan et al. | |
| 2006/0161218 A1 | 7/2006 | Danilov | |
| 2006/0163313 A1 | 7/2006 | Larson | |
| 2006/0282062 A1 | 12/2006 | Ishikawa et al. | |
| 2007/0088247 A1 | 4/2007 | Bliweis et al. | |
| 2007/0233222 A1 | 10/2007 | Roeder et al. | |
| 2007/0276466 A1 | 11/2007 | Lavelle et al. | |
| 2008/0027423 A1 | 1/2008 | Choi et al. | |
| 2008/0051804 A1 | 2/2008 | Cottler et al. | |
| 2008/0065011 A1 | 3/2008 | Marchand et al. | |
| 2008/0212416 A1 | 9/2008 | Polonio et al. | |
| 2008/0262468 A1 | 10/2008 | Clifford et al. | |
| 2008/0262508 A1 | 10/2008 | Clifford et al. | |
| 2008/0262510 A1 | 10/2008 | Clifford | |
| 2009/0163828 A1 | 6/2009 | Turner et al. | |
| 2009/0171271 A1 | 7/2009 | Webster et al. | |
| 2009/0209972 A1 | 8/2009 | Loushin et al. | |
| 2009/0299344 A1 | 12/2009 | Lee et al. | |
| 2009/0299379 A1 | 12/2009 | Katz et al. | |
| 2010/0041447 A1 | 2/2010 | Graylin | |
| 2010/0048978 A1 | 2/2010 | Sing et al. | |
| 2010/0061581 A1 | 3/2010 | Soetejo et al. | |
| 2010/0198135 A1 | 8/2010 | Morriss et al. | |
| 2010/0217296 A1 | 8/2010 | Morriss et al. | |
| 2010/0274188 A1 | 10/2010 | Chang et al. | |
| 2010/0324488 A1 | 12/2010 | Smith | |
| 2011/0015645 A1* | 1/2011 | Liu | A61F 11/002 606/109 |
| 2011/0022069 A1 | 1/2011 | Mitusiria | |
| 2011/0077579 A1 | 3/2011 | Harrison et al. | |
| 2011/0288559 A1 | 11/2011 | Shahoian | |
| 2012/0179187 A1 | 7/2012 | Loushin et al. | |
| 2012/0259337 A1* | 10/2012 | del Rio | A61B 17/1615 606/80 |
| 2012/0265097 A1 | 10/2012 | Melchiorri et al. | |
| 2012/0310145 A1 | 12/2012 | Clifford et al. | |
| 2013/0030456 A1 | 1/2013 | Assell et al. | |
| 2013/0090544 A1 | 4/2013 | Clifford et al. | |
| 2013/0158656 A1* | 6/2013 | Sutton | A61F 2/2436 623/2.11 |
| 2013/0231736 A1* | 9/2013 | Essinger | A61F 2/2418 623/2.11 |
| 2013/0338678 A1 | 12/2013 | Loushin et al. | |
| 2014/0031844 A1* | 1/2014 | Kusleika | A61B 17/32078 606/159 |
| 2014/0094733 A1 | 4/2014 | Clopp et al. | |
| 2014/0100584 A1 | 4/2014 | Konstorum et al. | |
| 2014/0194891 A1 | 7/2014 | Shahoian | |
| 2014/0200599 A1* | 7/2014 | Shiber | A61B 17/32075 606/159 |
| 2014/0276906 A1 | 9/2014 | Andreas et al. | |
| 2014/0277050 A1 | 9/2014 | Andreas et al. | |
| 2015/0051688 A1* | 2/2015 | Cummins | A61F 2/966 623/1.11 |
| 2015/0142029 A1 | 5/2015 | Fahn et al. | |
| 2015/0164695 A1 | 6/2015 | Liu et al. | |
| 2015/0209509 A1 | 7/2015 | O'Cearbhaill et al. | |
| 2015/0305944 A1 | 10/2015 | Kaplan et al. | |
| 2016/0038341 A1 | 2/2016 | Clopp et al. | |
| 2016/0038342 A1 | 2/2016 | Van et al. | |
| 2016/0045369 A1 | 2/2016 | Clopp | |
| 2016/0045370 A1 | 2/2016 | Andreas et al. | |
| 2016/0045371 A1 | 2/2016 | Girotra et al. | |
| 2016/0213519 A1 | 7/2016 | Andreas et al. | |
| 2017/0209310 A1 | 7/2017 | Girotra et al. | |
| 2017/0281230 A1 | 10/2017 | Andreas et al. | |
| 2018/0085563 A1 | 3/2018 | Clifford et al. | |

FOREIGN PATENT DOCUMENTS

| | | |
|---|---|---|
| DE | 19918288 A1 | 10/2000 |
| EP | 0214527 A1 | 3/1987 |
| FR | 2526656 | 11/1983 |
| JP | H07-116190 A | 5/1995 |
| WO | WO 1999/011175 A1 | 3/1999 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2009/105619 | 8/2009 |
| WO | WO 7011/008948 | 1/2011 |
| WO | WO 9014/075949 | 5/2014 |
| WO | WO 2014/143543 | 9/2014 |
| WO | WO 2014/158571 | 10/2014 |
| WO | WO 2016/022899 | 2/2016 |
| WO | WO 2016/025308 | 2/2016 |
| WO | WO 2016/025309 | 2/2016 |
| WO | WO 2016/025310 | 2/2016 |
| WO | WO 2016/025453 | 2/2016 |

OTHER PUBLICATIONS

First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, dated Sep. 3, 2008.
Written Opinion for International Application No. PCT/US2008/060779, dated Sep. 3, 2008.
International Preliminary Report on Patentability for International Application No. PCT/US2008/060779, dated Nov. 17, 2009.
Office Action for U.S. Appl. No. 11/749,729, dated May 26, 2011, 11 pages.
Office Action for U.S. Appl. No. 11/749,729, dated Jun. 17, 2010, 8 pages.

(56) References Cited

OTHER PUBLICATIONS

Office Action for U.S. Appl. No. 11/749,733, dated Jun. 10, 2009, 13 pages.
Office Action for U.S. Appl. No. 11/749,733, dated Dec. 2, 2008, 9 pages.
U.S. Appl. No. 61/085,360, filed Jul. 31, 2008.
International Search Report for International Application No. PCT/US2009/052395, dated Nov. 6, 2009.
Written Opinion for International Application No. PCT/US2009/052395, dated Nov. 6, 2009.
International Search Report and Written Opinion t for International Application No. PCT/US2010/058718, dated Feb. 17, 2011.
Written Opinion for International Application No. PCT/US2010/058718, dated Feb. 17, 2011.
U.S. Appl. No. 61/225,893, filed Jul. 15, 2009.
Patent Examination Report No. 1 for Australian Application No. 2010273372, dated Nov. 12, 2014, 2 pages.
First Office Action for Chinese Application No. 201080041755.6, dated Jul. 3, 2013.
Notification of Reasons for Refusal for Japanese Application No. 2012-520778, dated Feb. 18, 2014.
Communication of the Substantive Examination Report for Mexican Application No. MX/a/2012/000691, dated Apr. 24, 2014.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
International Search Report and Written Opinion for International Patent Application No. PCT/US2015/044179, dated Dec. 18, 2015, 15 pages.
International Search Report and Written Opinion for International Application No. PCT/US2014/018320, dated Jun. 2, 2014, 10 pages.
International Search Report and Written Opinion for International Application No. PCT/US2014/018347, dated Apr. 17, 2014, 9 pages.
Office Action for U.S. Appl. No. 14/455,465, dated Mar. 28, 2018, 10 pages.
International Search Report and Written Opinion for International Application No. PCT/US2015/044173, dated Oct. 12, 2015, 9 pages.
International Search Report and Written Opinion for International Application No. PCT/US2015/044177, dated Oct. 30, 2015, 10 pages.
International Search Report and Written Opinion for International Application No. PCT/US2015/044183, dated Nov. 4, 2015, 9 pages.
International Search Report and Written Opinion for International Application No. PCT/US2015/044610, dated Nov. 5, 2015, 12 pages.
International Search Report for International Application No. PCT/US2009/069388, dated Jun. 30, 2010.
Written Opinion for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).

Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., The "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Rhinology Products, Boston Medical Products, www.bosmed.com, pp. 1-16, received before Jan. 2015.

\* cited by examiner

TYMPANOSTOMY TUBE DELIVERY DEVICE WITH ELASTOMERIC BRAKE

CROSS-REFERENCE TO RELATED PATENT APPLICATIONS

This application is a divisional application of and claims priority to U.S. patent application Ser. No. 14/455,465, filed Aug. 8, 2014, entitled "Tympanostomy Tube Delivery Device With Elastomeric Brake," the contents of which are incorporated herein by reference in their entirety.

BACKGROUND

Some children may exhibit recurrent episodes of otitis media and/or otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012, the disclosure of which is incorporated by reference herein. Still additional exemplary pressure equalization tube delivery systems are disclosed in U.S. Pub. No. 2011/0015645, entitled "Tympanic Membrane Pressure Equalization Tube Delivery System," published Jan. 20, 2011, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
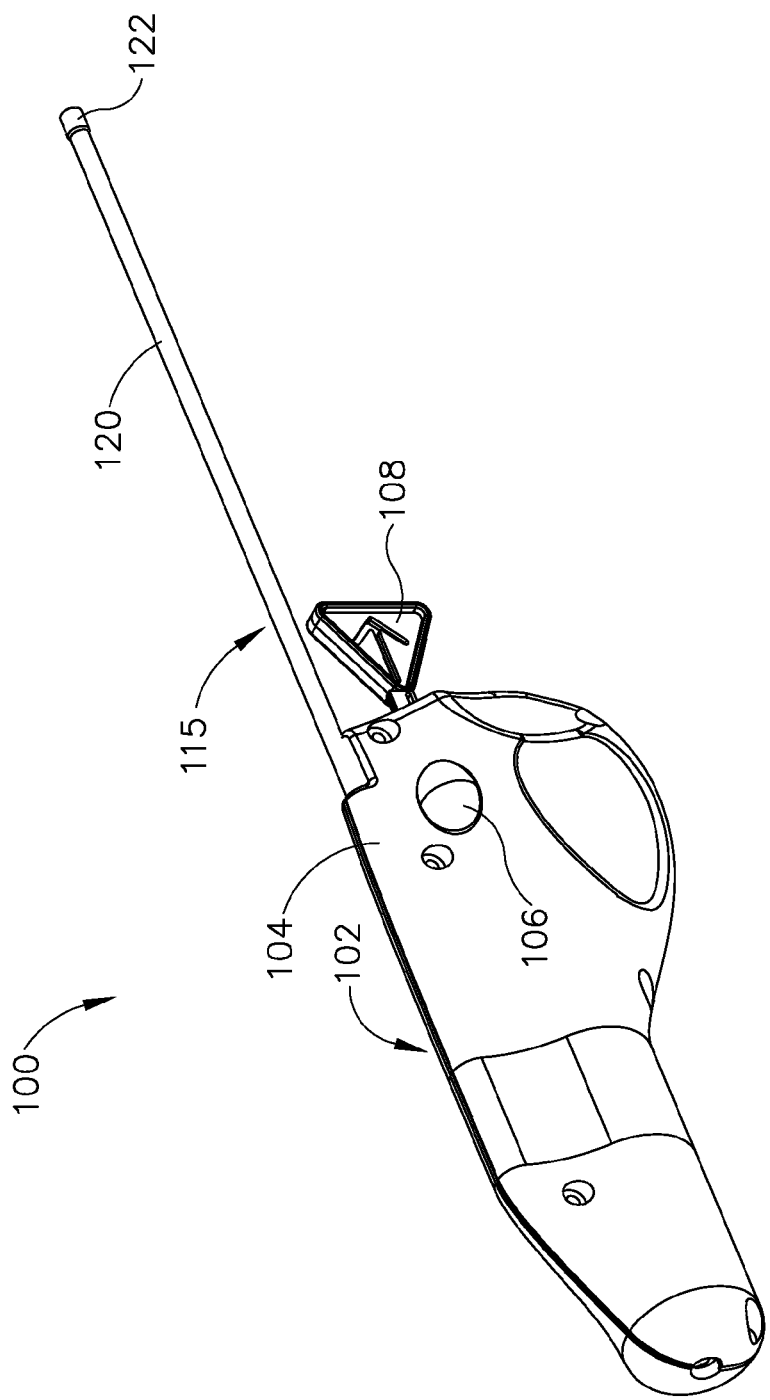
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Pressure Equalization Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary pressure equalization tube delivery device (PETDD) (100) that may be used in such procedures. It should be understood that PETDD (100) may be used with an endoscope to provide visualization of the tympanic membrane (TM) during use of PETDD (100). It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a handpiece (102) and a shaft assembly (115) extending distally from handpiece (102). Handpiece (102) is formed by two housing (104) halves that are joined together and that include internal features configured to support various components of PETDD (100) as will be described below. Handpiece (102) is configured to be handheld, such that an operator may fully operate PETDD (100) using a single hand. A pushbutton (106) is slidably disposed in housing (104) and includes exposed portions extending laterally from each side of handpiece (102). Pushbutton (106) is operable to be pushed along a path that is transverse to handpiece (102) in order to actuate PETDD (100) as will be described in greater detail below. A pull-pin (108) extends distally from handpiece (102) and is configured to prevent pushbutton (106) from being actuated, thereby preventing PETDD (100) from being actuated, so long as pull-pin (108) is disposed in handpiece (102). Pull-pin (108) is nevertheless removable from handpiece (102) to effectively unlock pushbutton (106) and thereby enable actuation of PETDD (100). Shaft assembly (115) of the present example includes a cannula (120) comprising an elongate tube having a clear tip member (122) at the distal end of cannula (120). Clear tip member (122) is configured to contact a patient's tympanic membrane (TM) while enabling visualization of the distal end of cannula (120). In some versions, tip member (122) is formed of a soft or elastomeric material such as rubber, soft plastic, etc. This may dampen vibrations that might otherwise be transmitted from cannula (120) to the patient's tympanic membrane (TM) during firing of PETDD (100). In addition or in the alternative, tip member (122) may include some other kind of dampening feature as will be apparent to those of ordinary skill in the art in view of the teachings herein.

Figure 2:
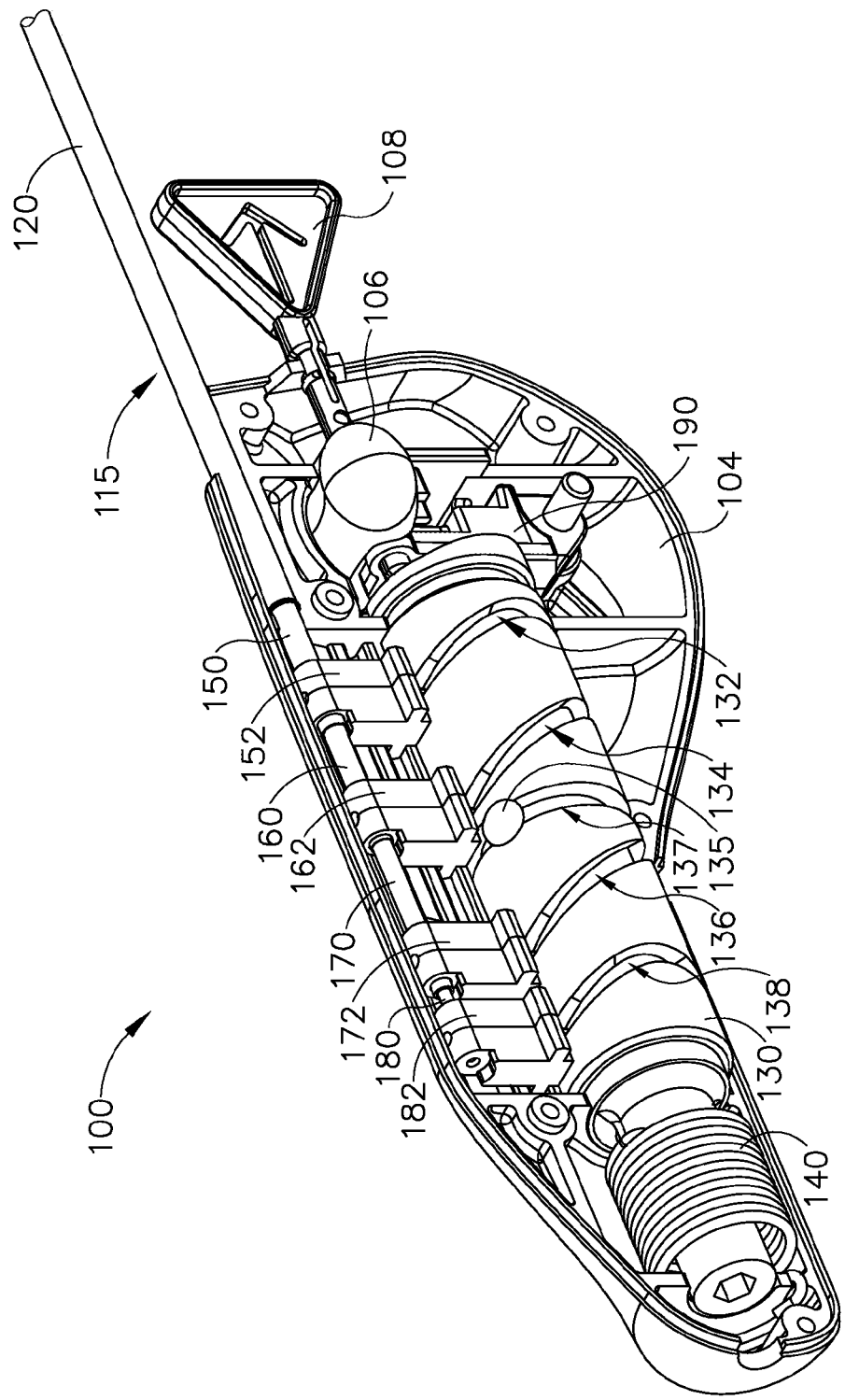
FIG. 2 depicts a perspective view of the PETDD of FIG. 1, with a housing half omitted.

As can be seen in FIG. 2, housing (104) supports a camshaft (130) and various other components. Camshaft (130) includes a dilator track (132), a shield tube track (134), a stopper track (137), a pusher track (136), and a piercer track (138). Tracks (132, 134, 136, 137, 138) are formed as recesses in camshaft (130) and each track (132, 134, 136, 137, 138) has a unique configuration in order to provide a particular sequence of operation of translating components as will be described in greater detail below. A torsion spring (140) is coupled to the proximal end of camshaft (130). Torsion spring (140) is also grounded against housing (104). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). As will be described in greater detail below (200), a trigger mechanism selectively resists such rotation. While torsion spring (140) is used to bias camshaft (130) in the present example, it should be understood that any other suitable types of components may be used to bias camshaft (130).

Figure 3:
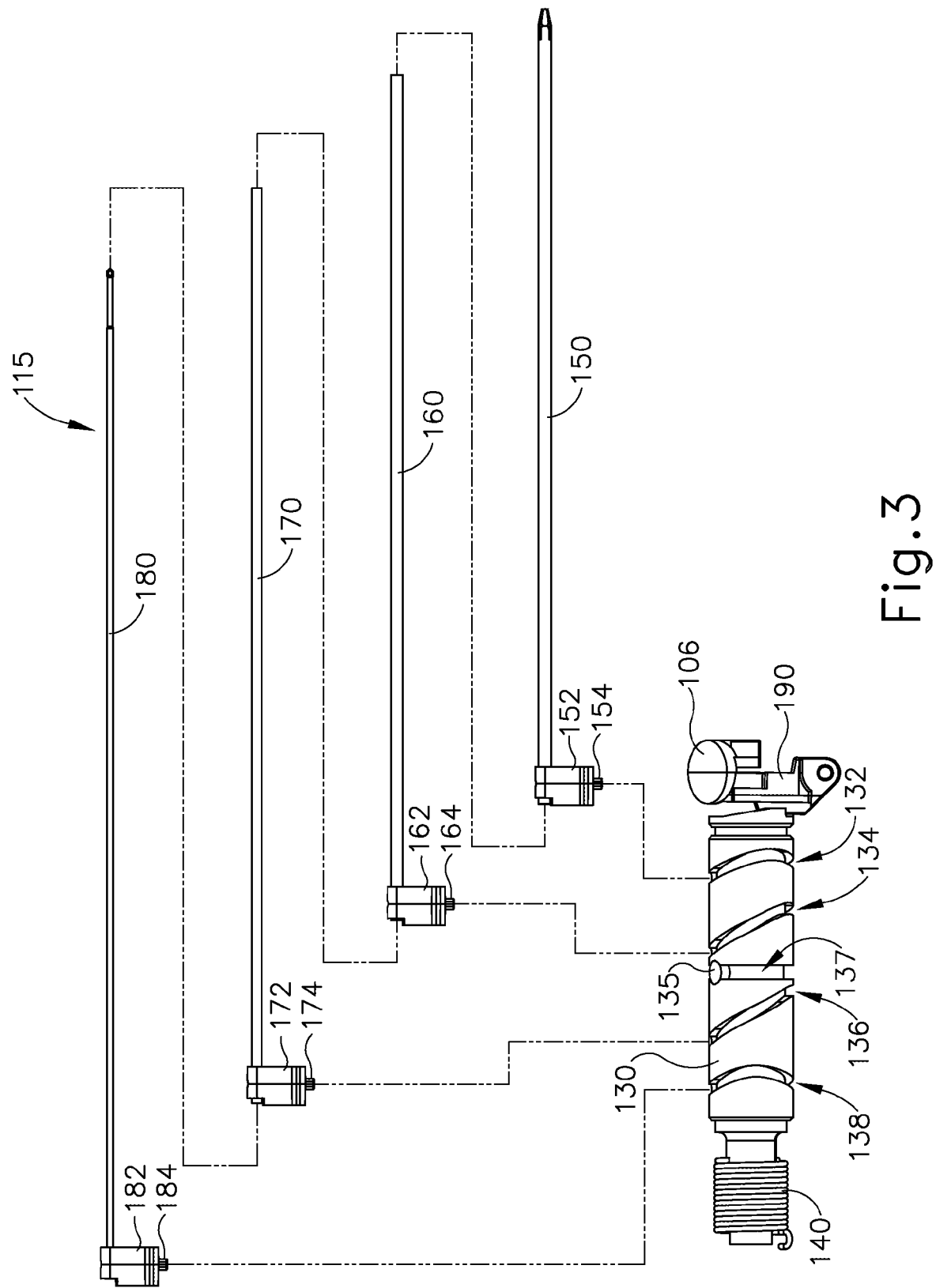
FIG. 3 depicts an exploded elevational view of actuation features of the PETDD of FIG. 1.

As shown in FIG. 3, various components are engaged with camshaft (130) and are thereby actuated by rotation of camshaft (130). In particular, a dilator tube (150), a shield tube (160), a pusher tube (170), and a piercer (180) are all engaged with camshaft (130). Tubes (150, 160, 170) and piercer (180) are all coaxially disposed within cannula (120) of shaft assembly (115). Piercer (180) is coaxially and slidably disposed within pusher tube (170), which is coaxially and slidably disposed within shield tube (160), which is coaxially and slidably disposed within dilator tube (150), which is coaxially and slidably disposed within cannula (120). Tubes (150, 160, 170) and piercer (180) all translate relative to cannula (120) in a particular sequence in order to deploy a PE tube as will be described in greater detail below. This sequence is driven by rotation of camshaft (130).

A cam follower (152) is fixedly secured to the proximal end of dilator tube (150). Cam follower (152) includes a laterally projecting pin (154) that is disposed in dilator track (132), such that rotation of camshaft (130) causes cam follower (152) and dilator tube (150) to translate. Similarly, a cam follower (162) is fixedly secured to the proximal end of shield tube (160). Cam follower (162) includes a laterally projecting pin (164) that is disposed in shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that is disposed in pusher tube track (136), such that rotation of camshaft (130) causes cam follower (172) and pusher tube (170) to translate. Finally, a cam follower (182) is fixedly secured to the proximal end of piercer (180). Cam follower (182) includes a laterally projecting pin (184) that is disposed in piercer track (138), such that rotation of camshaft (130) causes cam follower (182) and piercer (180) to translate. Stopper track (137) is simply annular in this example and includes a fixed elastomeric plug (135). An inwardly protruding boss (not shown) of housing (104) is disposed in stopper track (137). This boss remains disposed in stopper track (137) during rotation of camshaft (130).

Figure 4:
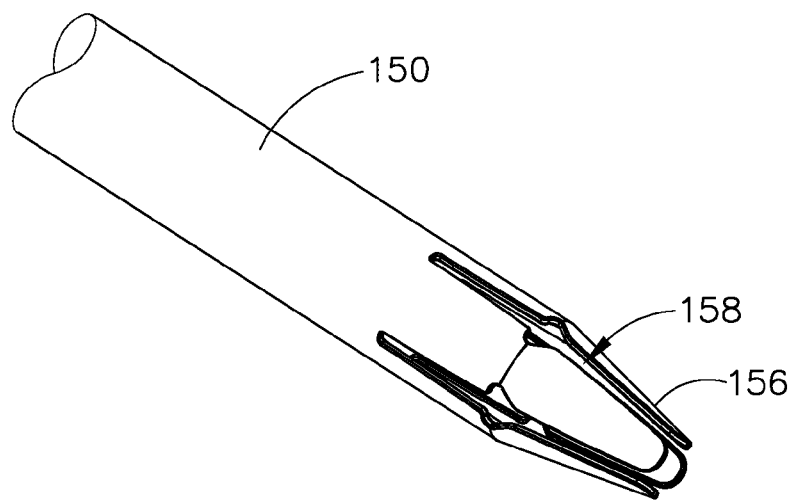
FIG. 4 depicts a perspective view of the distal end of a dilator of the actuation features of FIG. 3.
Figure 5:
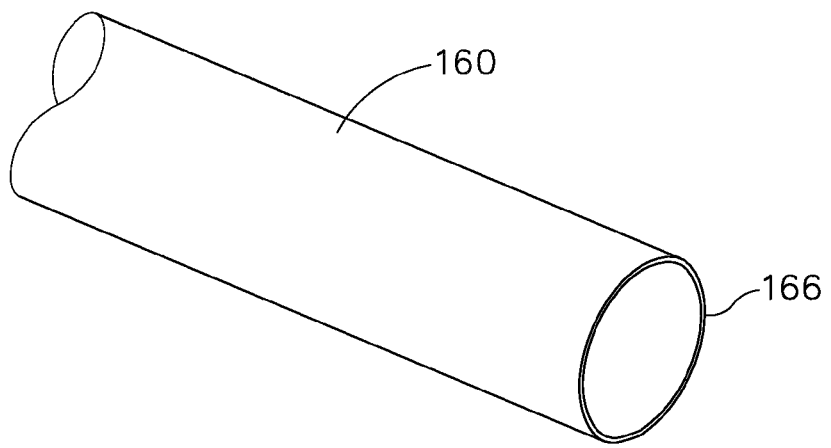
FIG. 5 depicts a perspective view of the distal end of a shield tube of the actuation features of FIG. 3.
Figure 6:
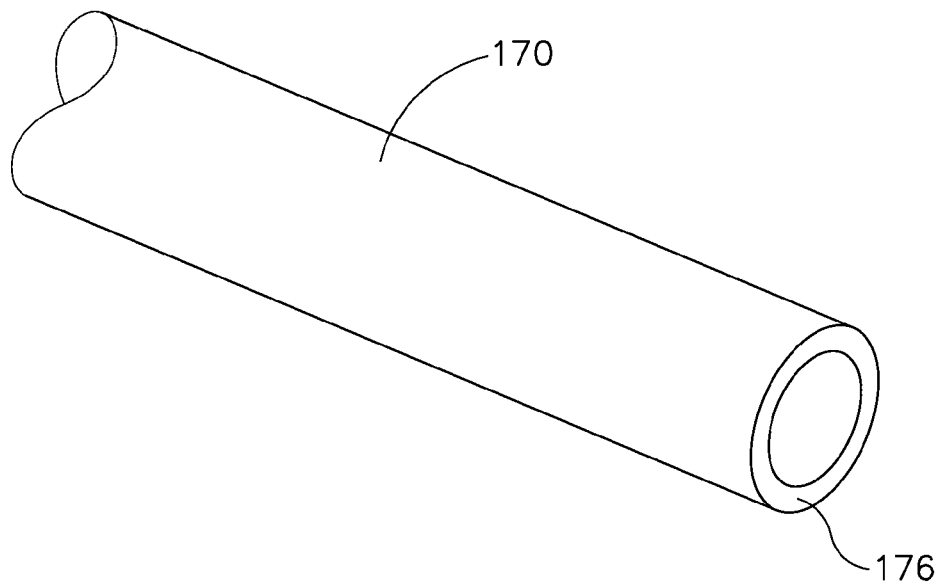
FIG. 6 depicts a perspective view of the distal end of a pusher of the actuation features of FIG. 3.
Figure 7:
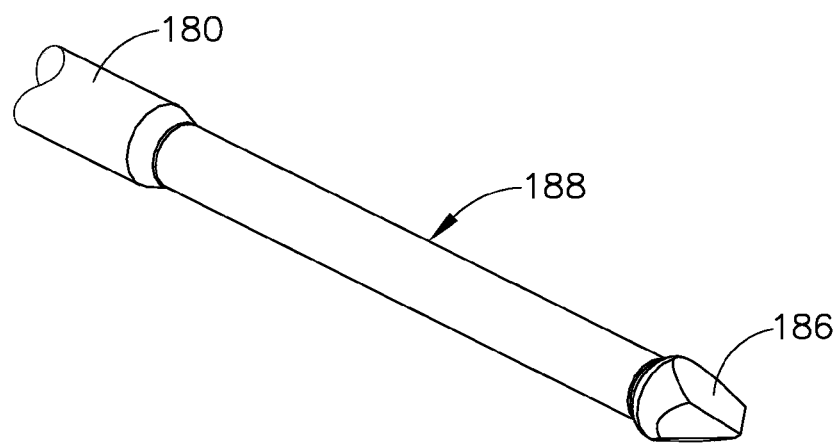
FIG. 7 depicts a perspective view of the distal end of a piercer of the actuation features of FIG. 3.

As shown in FIG. 4, the distal end of dilator tube (150) includes a plurality of generally flexible leaves (156) that are separated by longitudinally extending gaps (158). Leaves (156) are resiliently biased to assume the inwardly deflected positioning shown in FIG. 4; but are operable to flex outwardly from this positioning as will be described in greater detail below. As shown in FIG. 5, the distal end of shield tube (160) simply includes a circular edge (166). As shown in FIG. 6, the distal end of pusher tube (170) includes a distal face (176). In the present example, the difference between the inner diameter of pusher tube (170) and the outer diameter of pusher tube (170) is greater than the difference between the inner diameter of shield tube (160) and the outer diameter of shield tube (160). Thus, distal face (176) presents a more prominent contact surface than circular edge (166). As shown in FIG. 7, the distal end of piercer (180) includes a sharp, multi-faceted piercer tip (186) that is configured to pierce through a patient's tympanic membrane (TM). In the present example, piercer (180) also includes a neck-down region (188) having a reduced diameter.

Figure 8:
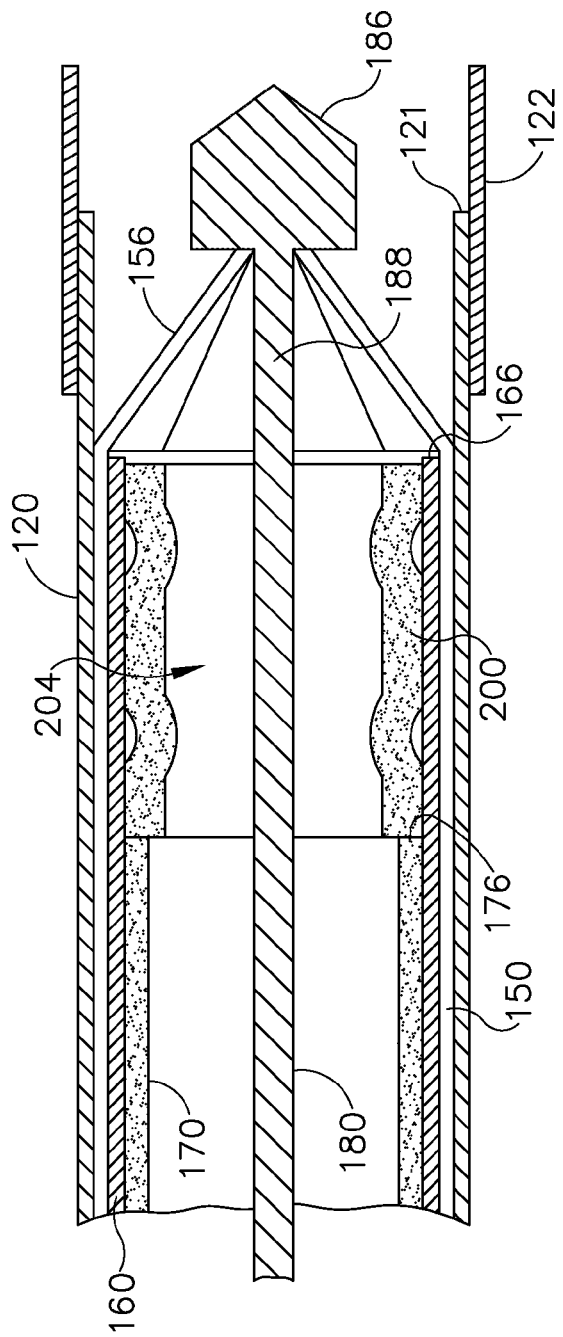
FIG. 8 depicts a cross-sectional side view of the actuation features of FIG. 3 with an exemplary pressure equalization (PE) tube.

FIG. 8 shows the positioning of tubes (150, 160, 170), piercer (180), and PE tube (200) within cannula (120) before camshaft (130) starts rotating from a home position. As shown, piercer tip (186) of piercer (180) is positioned distal to leaves (156) of dilator tube (150), such that leaves (156) are positioned about neck-down region (188) of piercer (180). PE tube (200) is positioned within the distal end of shield tube (160), whose distal edge (166) is just proximal to leaves (156). Pusher tube (170) is proximal to PE tube (200), with distal face (176) of pusher tube (170) abutting the proximal end of PE tube (200). In the present example, PE tube (200) is resiliently biased to assume a rivet-like shape presenting transverse petals (208) and a flange (206) (see FIG. 17-20). However, PE tube (200) is compressed against this bias, thereby assuming a generally cylindraceous configuration, when PE tube (200) is disposed within shield tube (160) as shown in FIG. 8.

Figure 9:
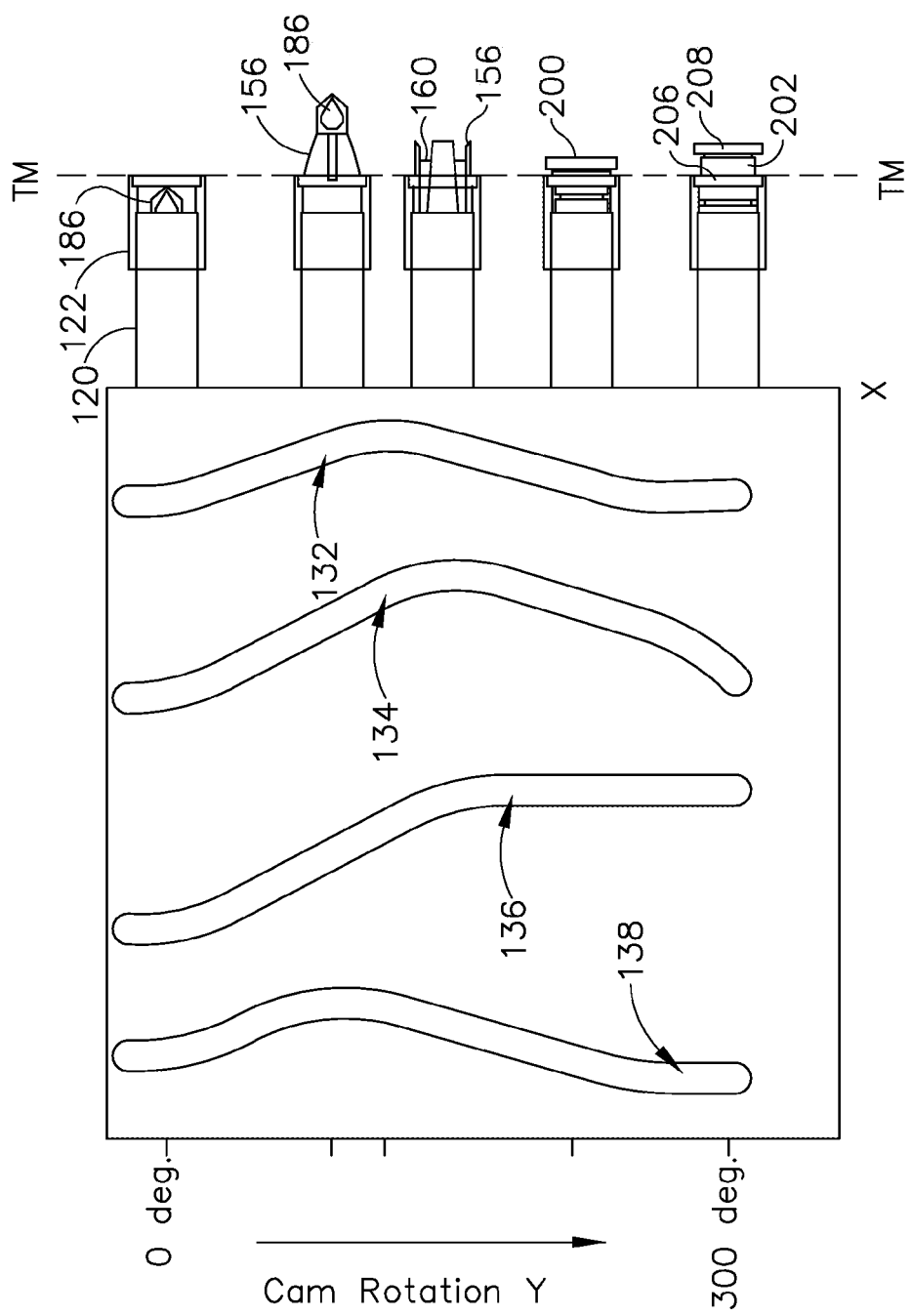
FIG. 9 depicts a displacement and operational diagram associated with the actuation features of FIG. 3.

FIG. 9 depicts a sequence of operation that occurs upon rotation of camshaft (130) from a home position to an actuated position, where tracks (132, 134, 136, 138) are shown developed into a flat pattern for purpose of illustration. The sequence starts at the top region of FIG. 9, which shows the distal end of clear tip member (122) contacting the patient's tympanic membrane (TM). At this stage, tubes (150, 160, 170), piercer (180), and PE tube (200) are at the positions shown in FIG. 8. Once camshaft (130) starts rotating at the urging of torsion spring (140), pins (154, 164, 174, 184) begin to ride along their respective tracks (132, 134, 136, 138), such that piercer tip (186) and leaves (156) are driven distally through the patient's tympanic membrane (TM). While not directly shown in FIG. 8, it should be understood that tubes (160, 170) are also driven distally during this transition, though tubes (160, 170) remain proximal to clear tip member (122) at this stage. As camshaft (130) continues to rotate, piercer (180) begins retracting proximally while tubes (160, 170) continue to advance distally. As shown, shield tube (160) spreads leaves (156) outwardly from their default positions. This further dilates the puncture site in the tympanic membrane (TM). Shield tube (160) continues to contain PE tube (200) at this stage. As camshaft (130) continues to rotate, piercer (180) and dilator (150) retract proximally behind clear tip member (122). Shield tube (160) also begins to retract proximally, while pusher tube (170) remains longitudinally stationary. This relative movement uncovers the distal end of PE tube (200), such that the resilient bias of petals (208) causes petals (208) to flex to transverse positions, thereby effectively forming a flange on the far side of the tympanic membrane (TM). Piercer (180) eventually returns to the fully proximal position, dilator (170) eventually returns to the fully proximal position, and pusher tube (170) eventually reaches a fully distal position. As camshaft (130) continues to rotate, shield tube (160) continues to retract proximally while pusher tube (170) remains longitudinally stationary. This relative movement uncovers the proximal end of PE tube (200), such that the resilient bias of PE tube (200) is allowed to form flange (206) on the near side of the tympanic membrane (TM).

Camshaft (130) stops rotating when the inwardly protruding boss of housing (104) engages plug (135) in stopper track (137). The elastomeric nature of plug (135) provides a relatively soft stop, such that plug (135) acts as a damper. This may reduce jolting of PETDD (100) when camshaft (130) comes to a stop and/or may prevent camshaft (130) from making a popping or snapping sound when camshaft (130) comes to a stop. Upon completion of the above described sequence shown in FIG. 9, cannula (120) is withdrawn from the patient's ear, leaving the actuated PE tube (200) in place in the patient's tympanic membrane (TM). Petals (208) and flange (206) cooperate to maintain the position of PE tube (200) in TM, while the passageway (204) formed by the interior of PE tube (200) (see FIGS. 8 and 17-20) provides a path for fluid communication (e.g., venting) between the patient's middle ear and outer ear. This fluid path further provides pressure equalization between the patient's middle ear and outer ear and/or promotes drainage of fluid from the middle ear via the Eustachian tube.

Figure 14:
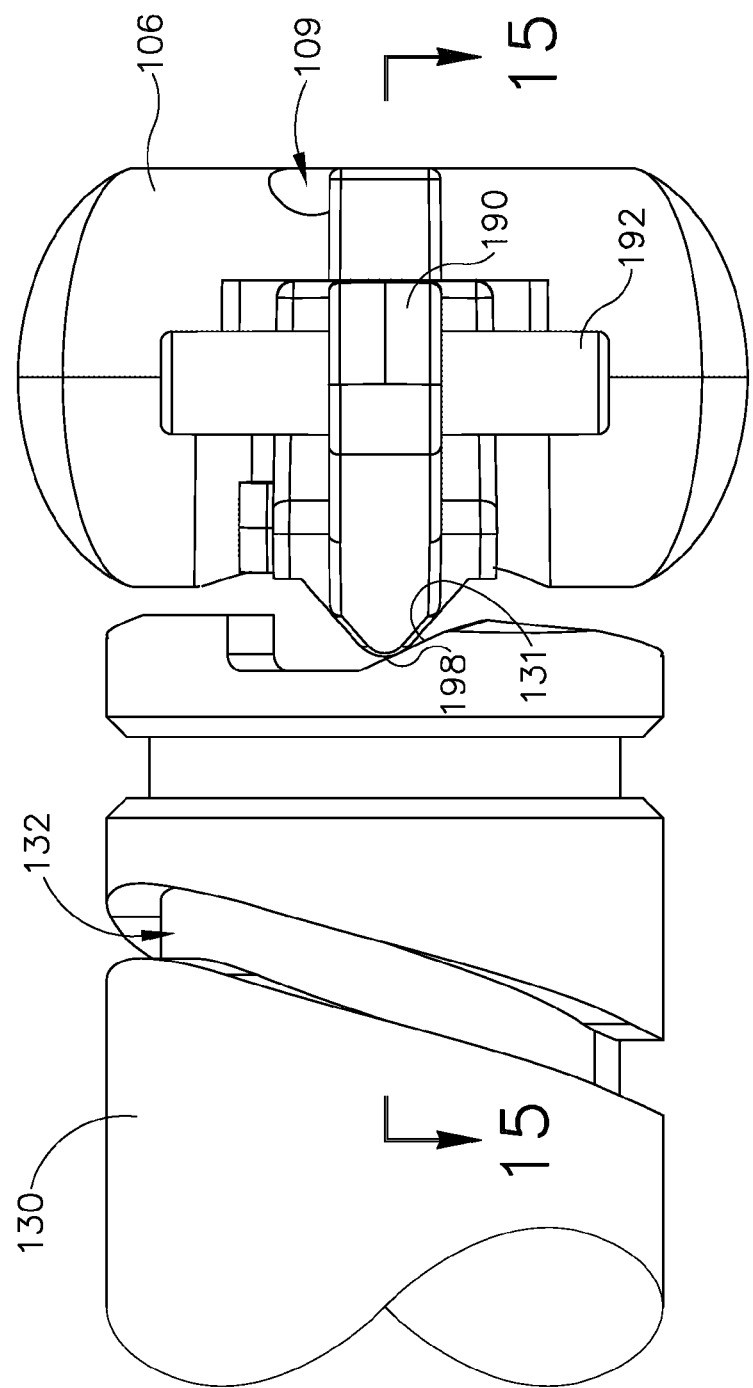
FIG. 14 depicts a bottom plan view of the trigger mechanism of FIG. 10, showing the pawl engaged with the camshaft.
Figure 15A:
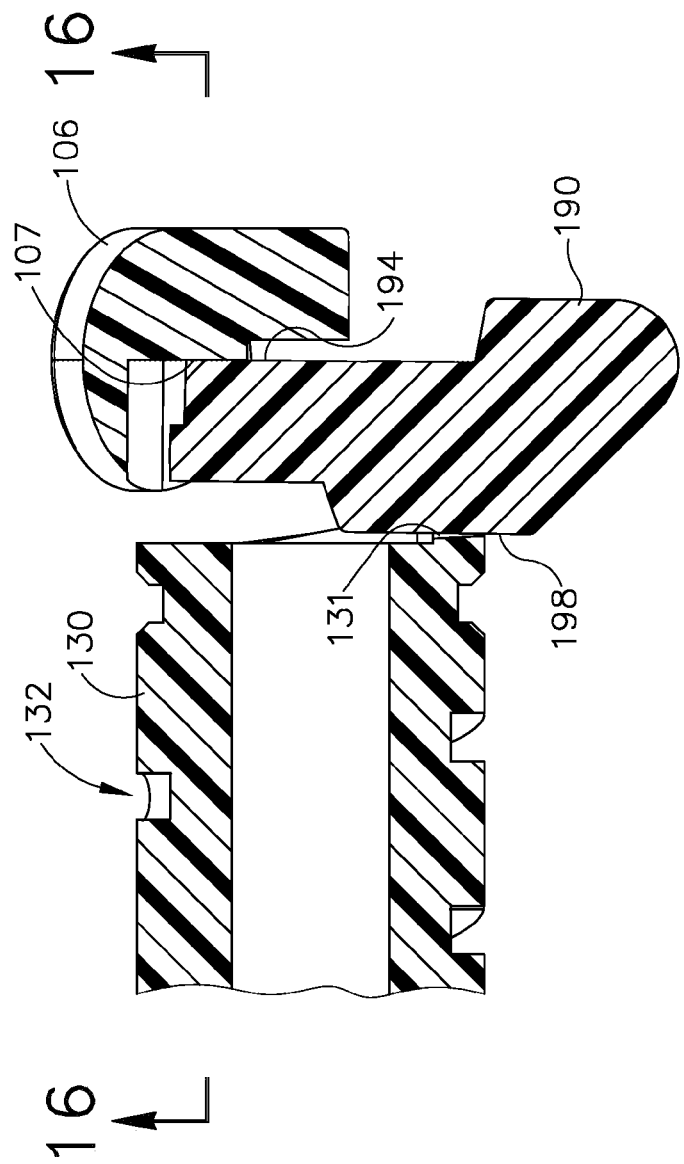
FIG. 15A depicts a cross-sectional view of the trigger mechanism of FIG. 10, taken along line 15-15 of FIG. 14, showing the pawl engaged with the camshaft.
Figure 15B:
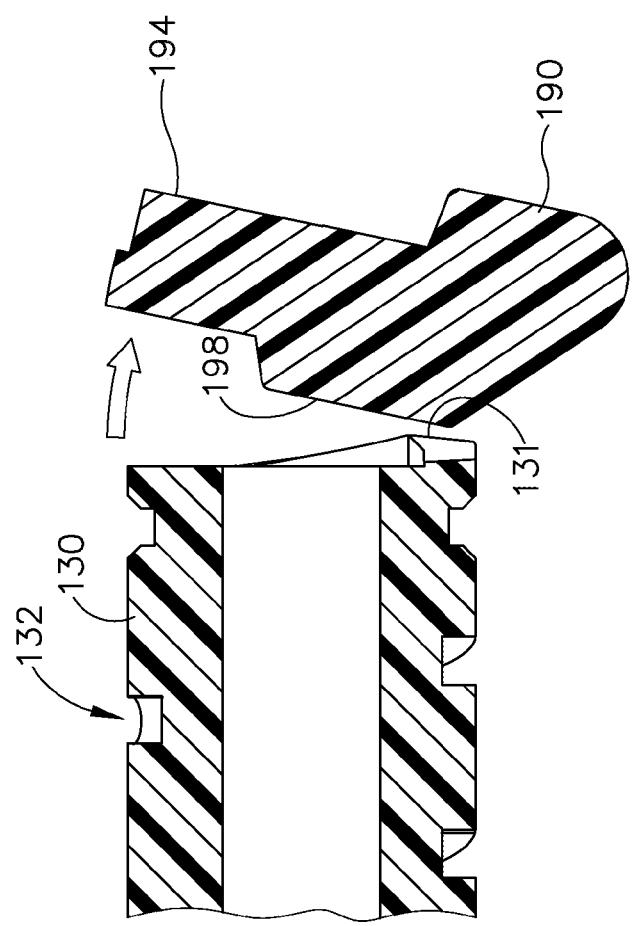
FIG. 15B depicts a cross-sectional view of the trigger mechanism of FIG. 10, taken along line 15-15 of FIG. 14, showing the pawl disengaged from the camshaft, with the button actuator omitted.
Figure 16B:
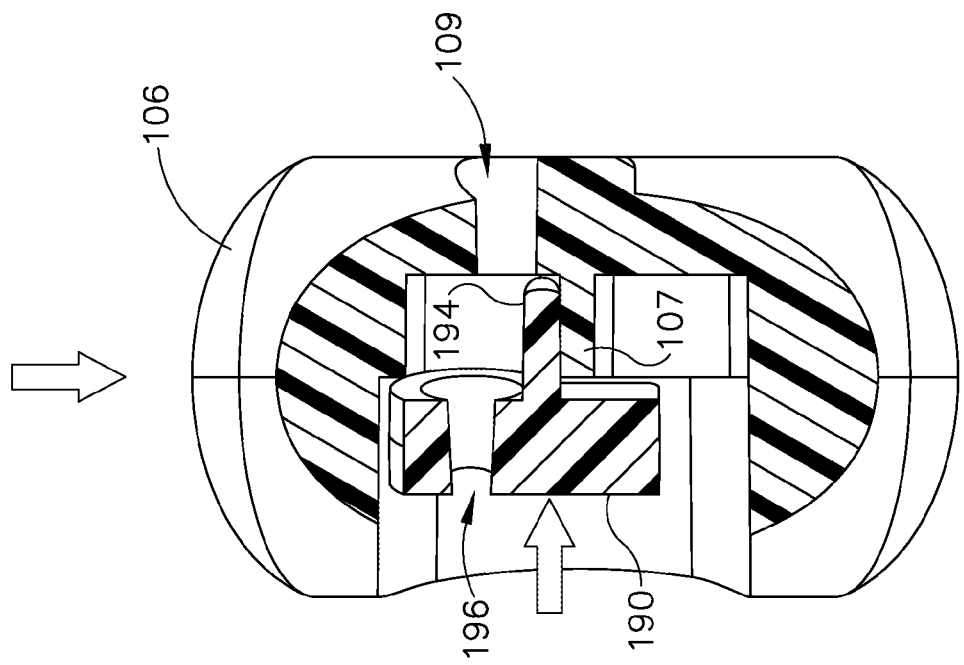
FIG. 16B depicts a cross-sectional view of the pawl and button actuator of FIGS. 11 and 13, taken along line 16-16 of FIG. 15A, showing the button actuator translated laterally to enable movement of the pawl.
Figure 16A:
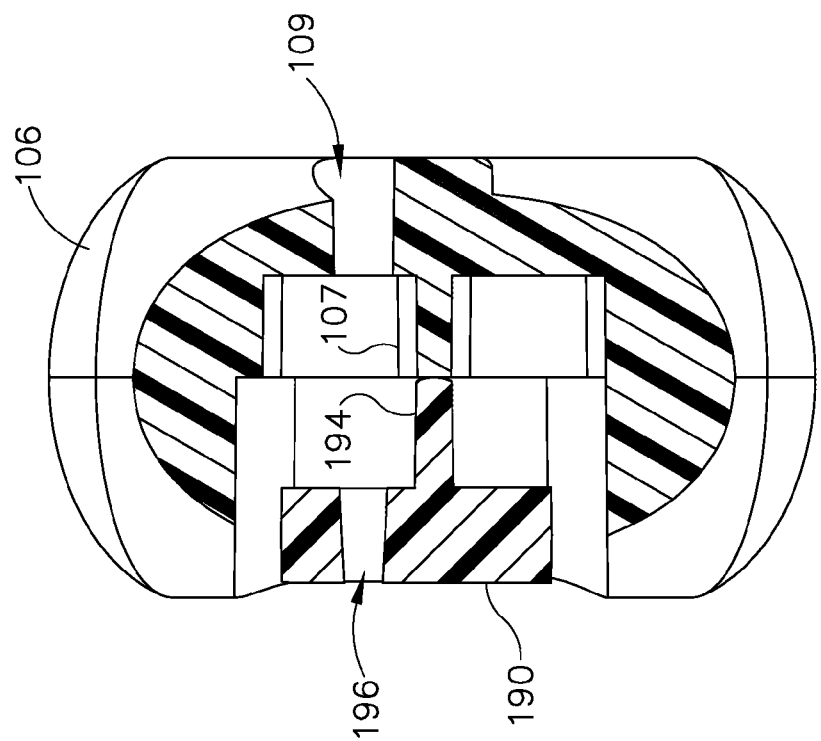
FIG. 16A depicts a cross-sectional view of the pawl and button actuator of FIGS. 11 and 13, taken along line 16-16 of FIG. 15A, showing the button actuator arresting the pawl.
Figure 17:
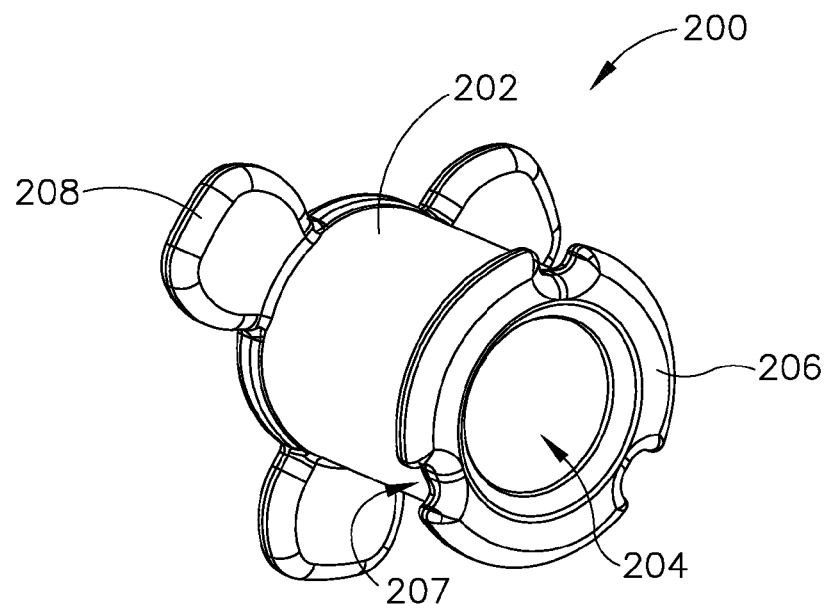
FIG. 17 depicts a perspective view of the proximal side of an exemplary PE tube suitable for delivery by the PETDD of FIG. 1.
Figure 18:
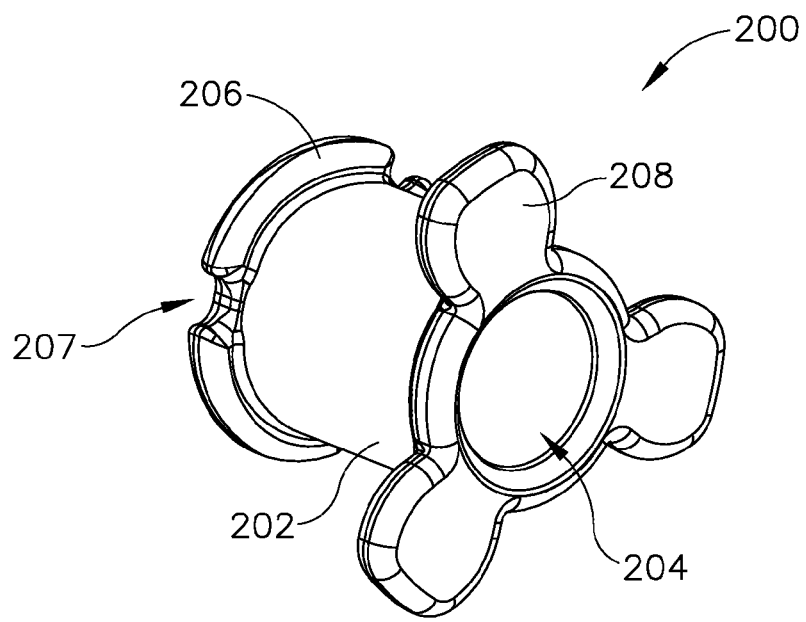
FIG. 18 depicts a perspective view of the distal side of the PE tube of FIG. 17.
Figure 19:
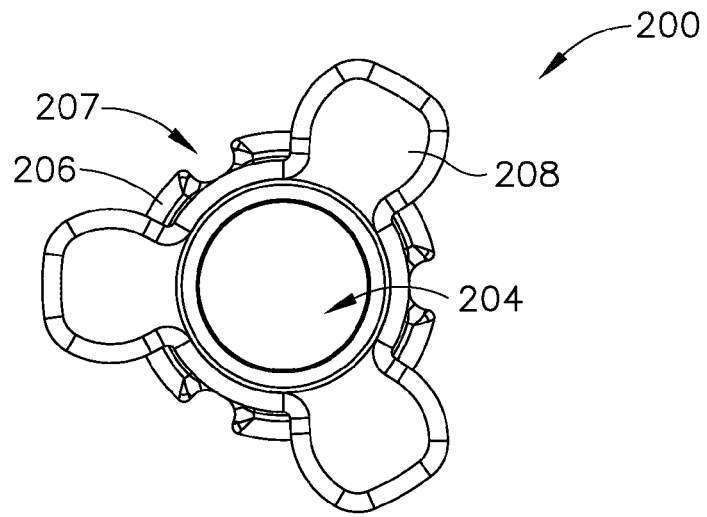
FIG. 19 depicts a distal elevational view of the PE tube of FIG. 17.
Figure 20:
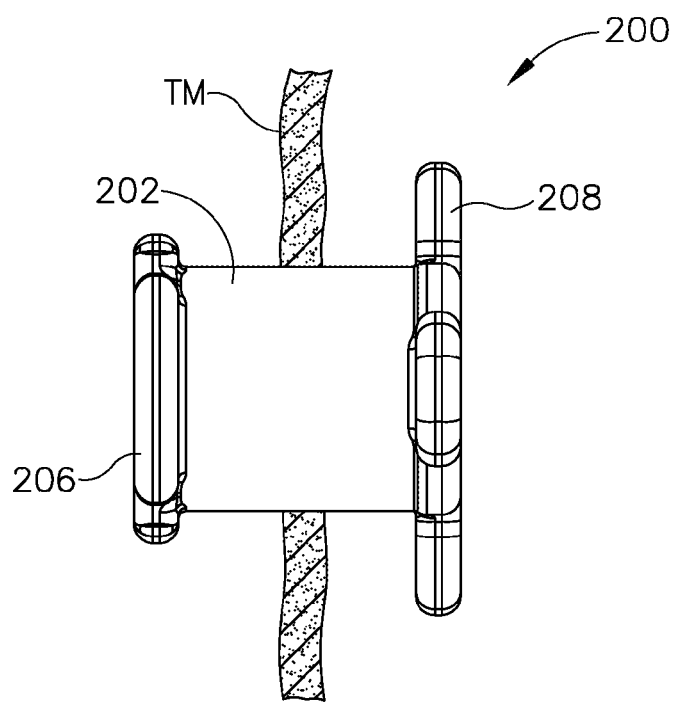
FIG. 20 depicts a side elevational view of the PE tube of FIG. 17, positioned within a tympanic membrane.

As noted above, PETDD (100) of the present example includes a trigger mechanism that is configured to selectively resist rotation of camshaft (130) by torsion spring (140). As best seen in FIGS. 10-16B, the trigger mechanism of this example comprises a pawl member (190) that selectively engages pushbutton (106) and camshaft (130). Pawl member (190) includes laterally extending pins (192) that couple pawl member (190) with housing (104). While housing (104) prevents pawl member (190) from moving laterally within housing (104), housing (104) permits pawl member (190) to pivot freely about pins (192) within housing (104). Pawl member (190) includes a distally facing boss rib (194) that extends vertically. Pawl member (190) also includes a pull-pin opening (196) and a proximally facing pawl ridge (198). Boss rib (194) is configured to selectively engage a proximally facing boss rib (107) of pushbutton (106) as will be described in greater detail below. Pull-pin opening (196) is configured to receive pull-pin (108), which assists to prevent pawl member (190) from pivoting about pins (192) when pull-pin (108) is disposed in pull-pin opening (196). Pawl ridge (198) includes chamfered lateral faces (199) and is configured to selectively engage a retention feature (131) of camshaft (130). In particular, when pawl member (190) is in a first position as shown in FIGS. 14, 15A, and 16A, pawl ridge (198) is engaged with retention feature (131) and prevents camshaft (130) from rotating despite the rotational bias provided by torsion spring (140). When pawl member (190) is pivoted to a second position as shown in FIGS. 15B and 16B, pawl ridge (198) disengages retention feature (131), enabling camshaft (130) to rotate under the influence of torsion spring (140) to provide the sequence of operation described above.

Figure 10:
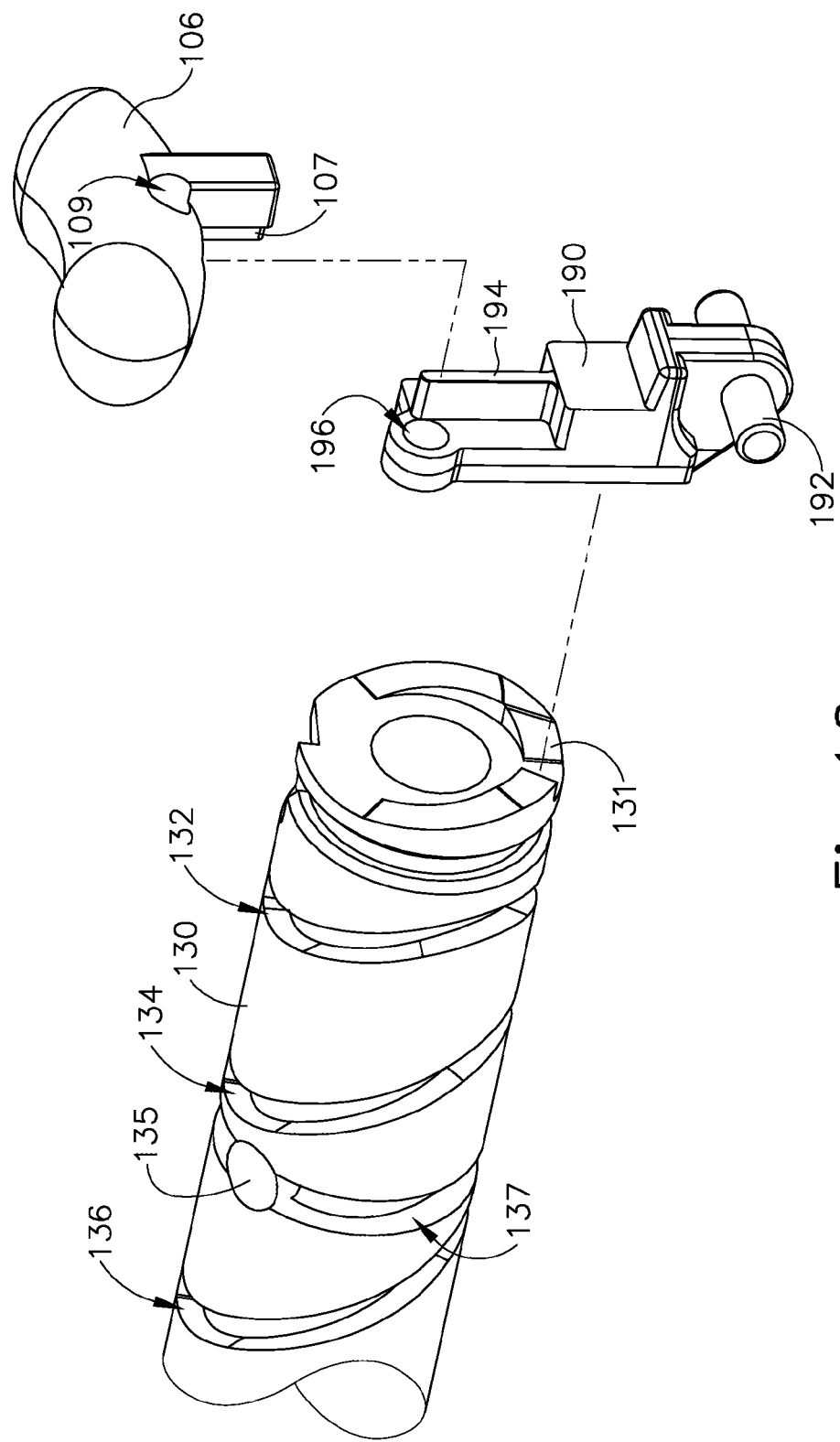
FIG. 10 depicts an exploded perspective view of a trigger mechanism of the actuation features of FIG. 3.
Figure 12:
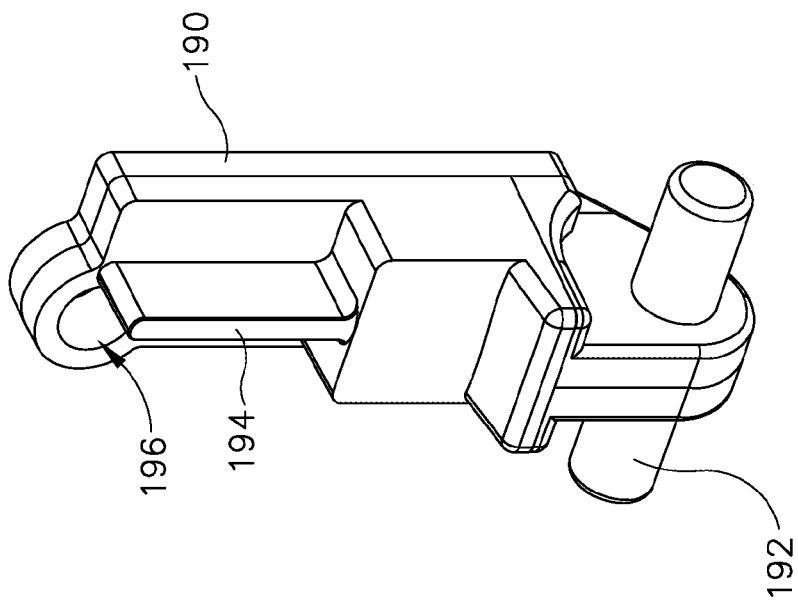
FIG. 12 depicts a perspective view of the distal side of the pawl of FIG. 11.
Figure 11:
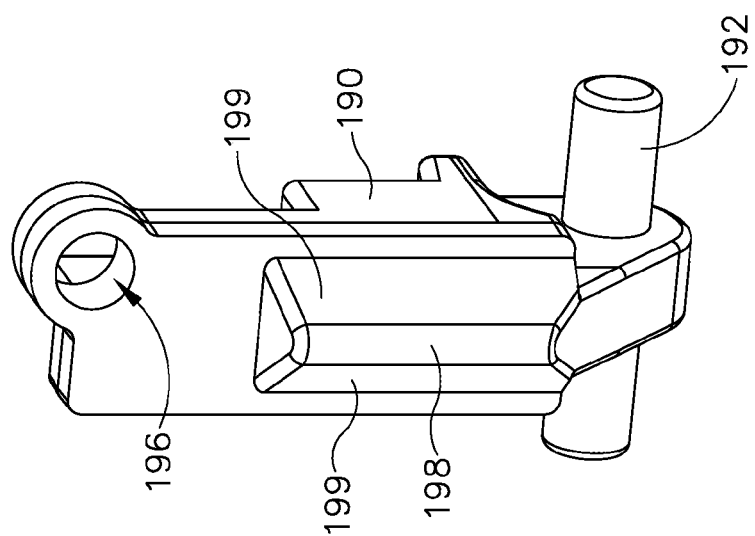
FIG. 11 depicts a perspective view of the proximal side of a pawl of the trigger mechanism of FIG. 10.
Figure 13:
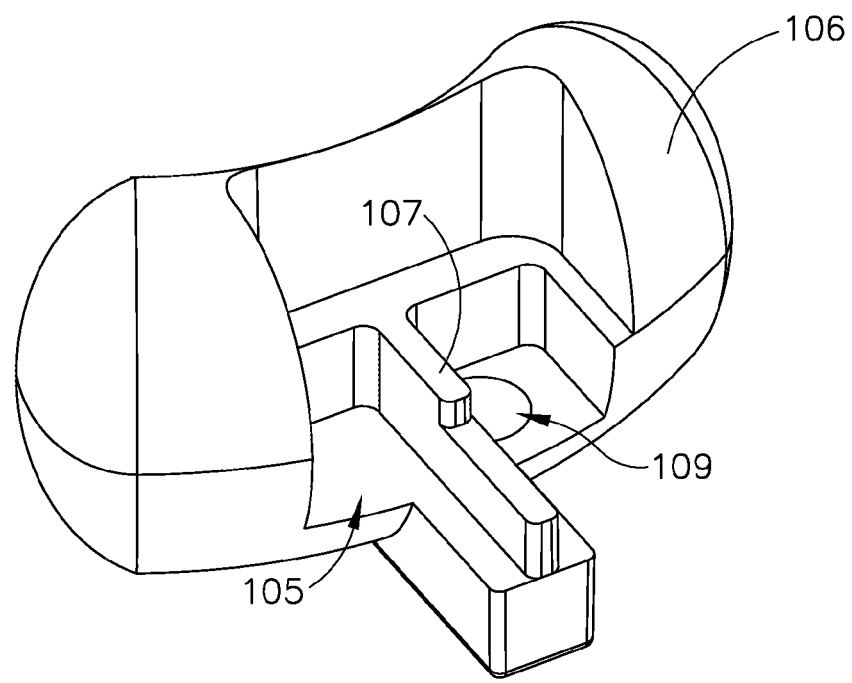
FIG. 13 depicts a perspective view of the proximal underside of a button actuator of the trigger mechanism of FIG. 10.

As best seen in FIGS. 10 and 13, pushbutton (106) includes a pull-pin opening (109) that is configured to receive pull-pin (108). Pushbutton (106) is prevented from translating laterally relative to housing (104) when pull-pin (108) is disposed within pull-pin opening (109). Pull-pin (108) thus provides a lockout for pushbutton (106). To unlock pushbutton (106), pull-pin (108) may be pulled distally out of housing (104). As noted above, pushbutton (106) also includes a proximally facing boss rib (107) that extends vertically. When pushbutton (106) is laterally centered within housing (104), boss rib (107) engages boss rib (194), as shown in FIGS. 15A and 16A. This engagement prevents pawl member (190) from pivoting distally about pins (192). Pushbutton (106) and pawl member (190) together thus effectively lock camshaft (130) when pushbutton (106) is laterally centered within housing (104).

When pushbutton (106) is laterally displaced relative to housing (104) (i.e., when a user depresses an exposed portion of pushbutton (106) laterally relative to housing (104)), bosses (107, 194) disengage such that pushbutton (106) no longer blocks pivoting of pawl member (190). Due to the torsional bias of camshaft (130), the ramped configuration of retention feature (131), and the chamfered lateral faces (199) of pawl ridge (198), camshaft (130) forces pawl member (190) to pivot out of the way to the position shown in FIGS. 15B and 16B when pushbutton (106) is no longer blocking pawl member (190). This enables camshaft (130) to complete the operational drive sequence described above. While pushbutton (106) is depicted as being pushed in one lateral direction, it should be understood that the same triggering operation may be provided when pushbutton (106) is pushed in the opposite lateral direction from the center position. With portions of pushbutton (106) being exposed through housing (104) on each side of handpiece (102), this allows the operator to select which side of pushbutton (106) to press.

It should be understood that the foregoing components, features, and operabilities of PETDD (100) are merely illustrative examples. A PETDD (100) may include various other features in addition to or in lieu of those described above. By way of example only, any of the devices herein may also include one or more of the various features disclosed in any of the various references that are incorporated by reference herein. Some additional merely illustrative variations of PETDD (100) will be described in greater detail below, while other variations of PETDD (100) will be apparent to those of ordinary skill in the art in view of the teachings herein.

II. Exemplary Pressure Equalization Tube

FIGS. 17-20 show PE tube (200) in greater detail. PE tube (200) of this example includes a cylindraceous body (202) that defines a passageway (204). A flange (206) is located at the proximal end of body (202) while a set of petals (208) are located at the distal end of body (202). Flange (206) includes a plurality of inwardly directed recesses (207). Recesses (207) are configured to facilitate flexing of flange (206) from an outwardly extended position to a generally cylindraceous position where the material forming flange (206) extends longitudinally. While three recesses (207) are shown, it should be understood that any other suitable number of recesses (207) may be provided. Similarly, while three petals (208) are shown, it should be understood that any other suitable number of petals (208) may be provided.

PE tube (200) is formed of a resilient material that is biased to assume the rivet like configuration shown in FIGS. 17-20. However, flange (206) and petals (208) may be flexed inwardly toward the longitudinal axis of body (202) to provide PE tube (200) with a cylindraceous configuration. In particular, flange (206) and petals (208) may be flexed such that their outer surfaces are at the same radial distance from the longitudinal axis as the outer perimeter of body (202). This radial distance may be slightly less than the radial distance associated with the inner diameter of shield tube (160), such that PE tube (200) may collapse to fit within shield tube (160). When PE tube (200) is disposed in a tympanic membrane (TM), petals (208) are located medially (i.e., on the middle ear side) while flange (206) is located laterally (i.e., on the outer ear side). By way of example only, PE tube (200) may also be configured in accordance with at least some of the teachings of U.S. patent application Ser. No. 13/800,113, entitled "Tympanic Membrane Pressure Equalization Tube," filed on Mar. 13, 2013, published as U.S. Pub. No. 2014/0094733 on Apr. 3, 2014, the disclosure of which is incorporated by reference herein. Other suitable forms that PE tube (200) may take will be apparent to those of ordinary skill in the art in view of the teachings herein.

III. Exemplary Pressure Equalization Tube Delivery Instrument with Elastomeric Brake As noted above, of PETDD (100) includes a plug (135) and an inwardly protruding boss of housing (104) that cooperate to provide a relatively soft stop to rotating camshaft (130) when of PETDD (100) is fired. It should be understood that this may also reduce the noise that is transmitted to the patient's ear when PETDD (100) is fired, such that plug (135) provides sound dampening. It should also be understood that grease and/or some other material(s)

may be provided in track (137) and/or one or more of tracks (132, 134, 136, 138) to provide sound dampening when PETDD (100) is fired. In some instances, the stop provided by plug (135) and an inwardly protruding boss of housing (104) may be abrupt even if the stop is soft. Similarly, the dampening provided by grease may be somewhat inconsistent from one PETDD (100) to another PETDD (100). It may therefore be desirable to provide a stop that is both soft and relatively gradual; while also providing consistency in the dampening effect from one PETDD (100) to another PETDD (100). The examples described below may provide such results and/or other results.

Figure 21:
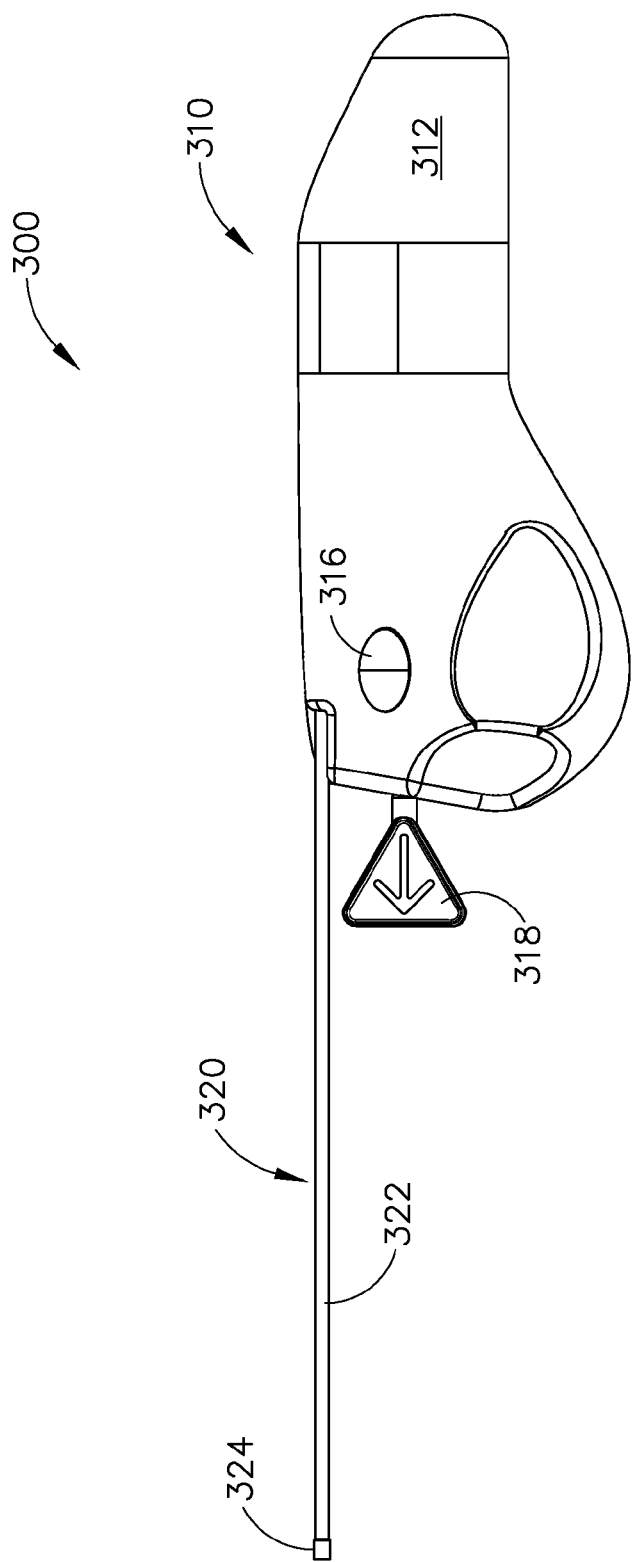
FIG. 21 depicts a side elevational view of an exemplary alternative PETDD.
Figure 22:
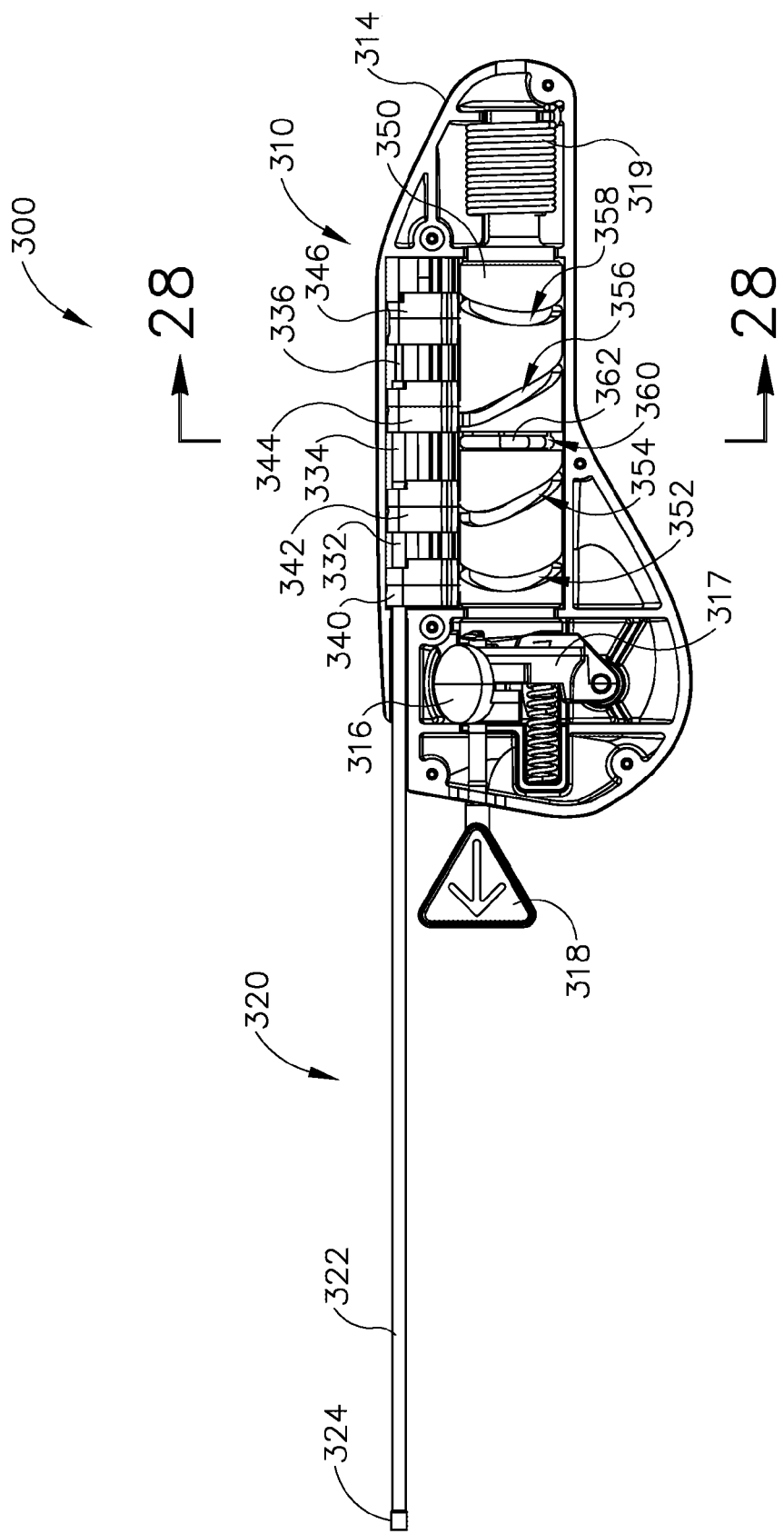
FIG. 22 depicts a side elevational view of the PETDD of FIG. 21, with a housing half removed.
Figure 23:
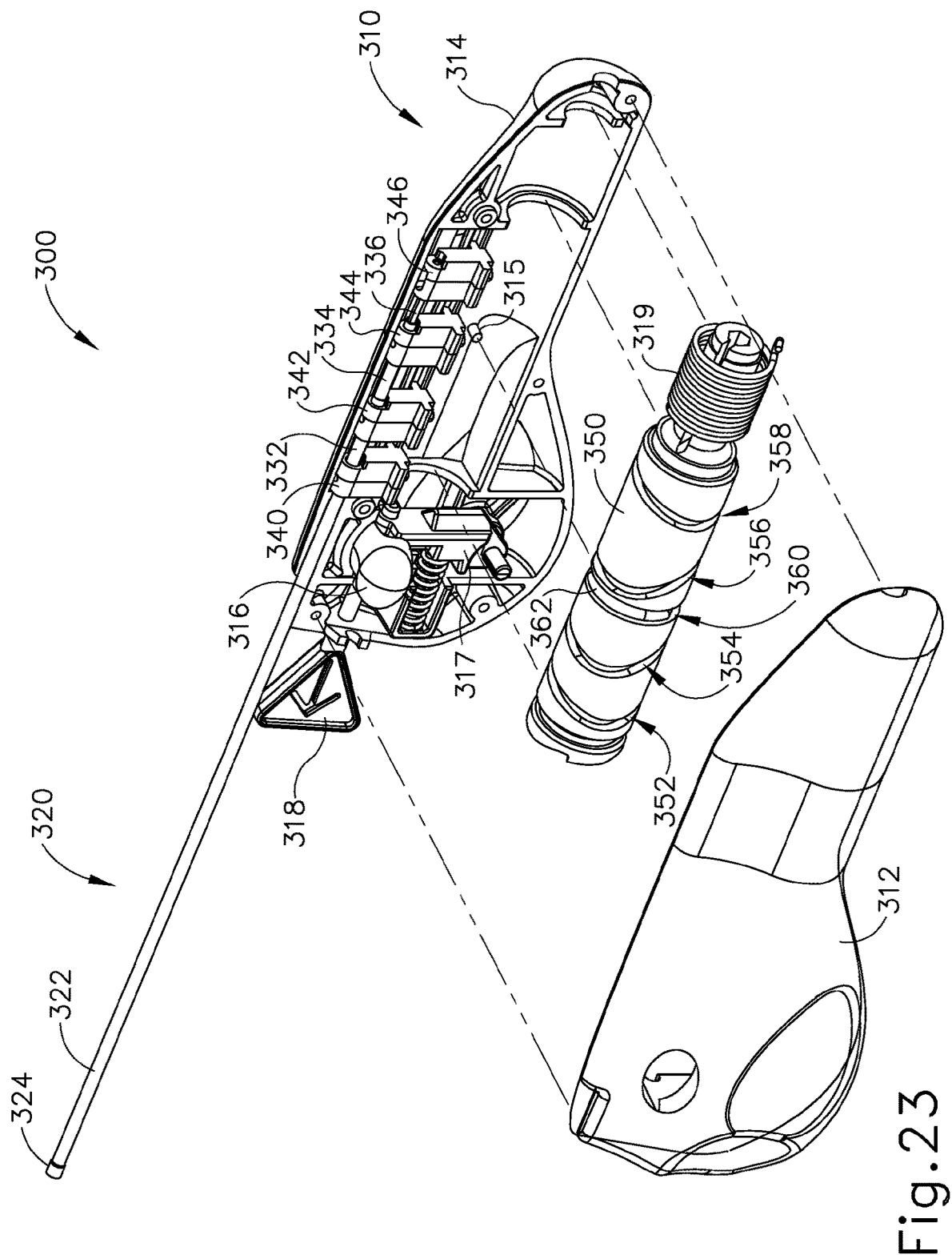
FIG. 23 depicts an exploded perspective view of the PETDD of FIG. 21.

FIGS. 21-23 show an exemplary alternative PETDD (300). PETDD (300) of this example is configured and operable identically to PETDD (100) described above, except for the differences discussed below. PETDD (300) of this example comprises a handpiece (310) and a shaft assembly (320) extending distally from handpiece (310). Handpiece (310) comprises a pair of housing halves (312, 314), a pushbutton (316), and a pull-pin (318). Shaft assembly (320) comprises an outer cannula (322) with a tip member (324) and a plurality of components coaxially disposed within outer cannula (322). In particular, these internal components of shaft assembly (320) include a dilator tube (not shown), a shield tube (332), a pusher tube (334), and a piercer (336). A respective cam follower (340, 342, 344, 346) is fixedly secured to the proximal end of each of these components. Cam followers (340, 342, 344, 346) are engaged with a camshaft (350), which is captured between housing halves (312, 314). Camshaft (350) includes a set of tracks (352, 354, 356, 358) that receive respective pins of cam followers (340, 342, 344, 346), providing engagement between camshaft (350) and cam followers (340, 342, 344, 346). Camshaft (350) is rotatable within handpiece (310) to drive cam followers (340, 342, 344, 346) to translate linearly in an operational sequence that is based on the configuration of tracks (352, 354, 356, 358). Camshaft (350) thereby actuates the components of shaft assembly (320) just like camshaft (130) actuates the components of shaft assembly (115) in PETDD (100) as described above. The actuated components of shaft assembly (320) may deploy a PE tube (200) from shaft assembly (320) just like the actuated components of shaft assembly (115) deploy a PE tube (200) as described above.

As best seen in FIGS. 22-23, a torsion spring (319) is secured to the proximal end of camshaft (350). Torsion spring (319) is mechanically grounded against one or both housing halves (312, 314). Torsion spring (319) is thus configured to provide a rotational bias to camshaft (350). A pawl member (317) is pivotably secured between housing halves (312, 314) and is configured to selectively engage the distal end of camshaft (350). Pawl member (317) is thus configured to selectively resist rotation of camshaft (350) as imposed by the resilient bias of torsion spring (319). Pushbutton (316) is coupled with pawl member (317) such that pushbutton (316) may be actuated to disengage pawl member (317) from camshaft (350). Pull-pin (318) selectively secures pawl member (317) in place. It should therefore be understood that torsion spring (319), pawl member (317), pushbutton (316), and pull-pin (318) may be configured and operable substantially similar to torsion spring (140), pawl member (190), pushbutton (106), and pull-pin (318) of PETDD (100) as described above. Of course, any other suitable components may be used to provide actuation of PETDD (300). Other suitable ways in which PETDD (300) may be actuated will be apparent to those of ordinary skill in the art in view of the teachings herein.

Figure 27:
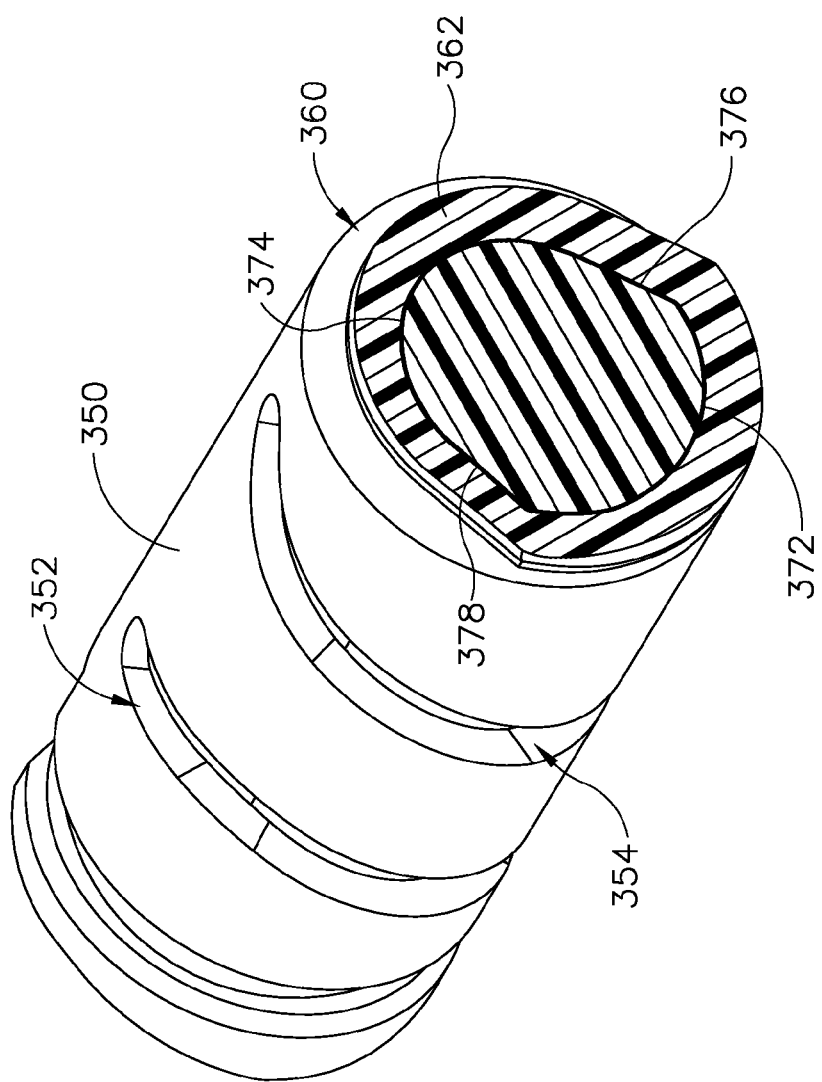
FIG. 27 depicts a perspective cross-sectional view of the camshaft of FIG. 25.
Figure 28A:
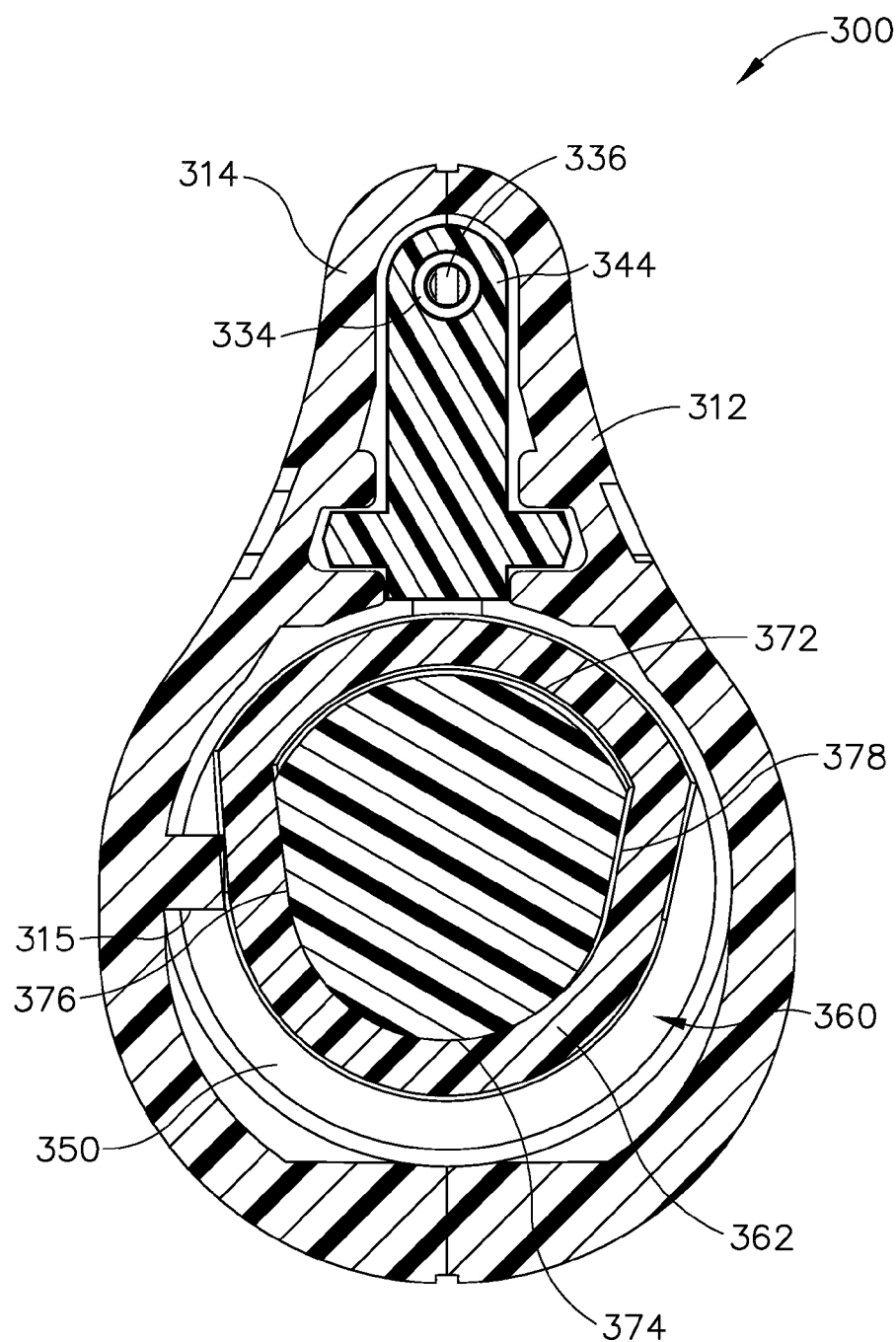
FIG. 28A depicts a cross-sectional end view of the PETDD of FIG. 21, taken along line 28-28 of FIG. 22, with the camshaft of FIG. 25 in an initial angular position.
Figure 28B:
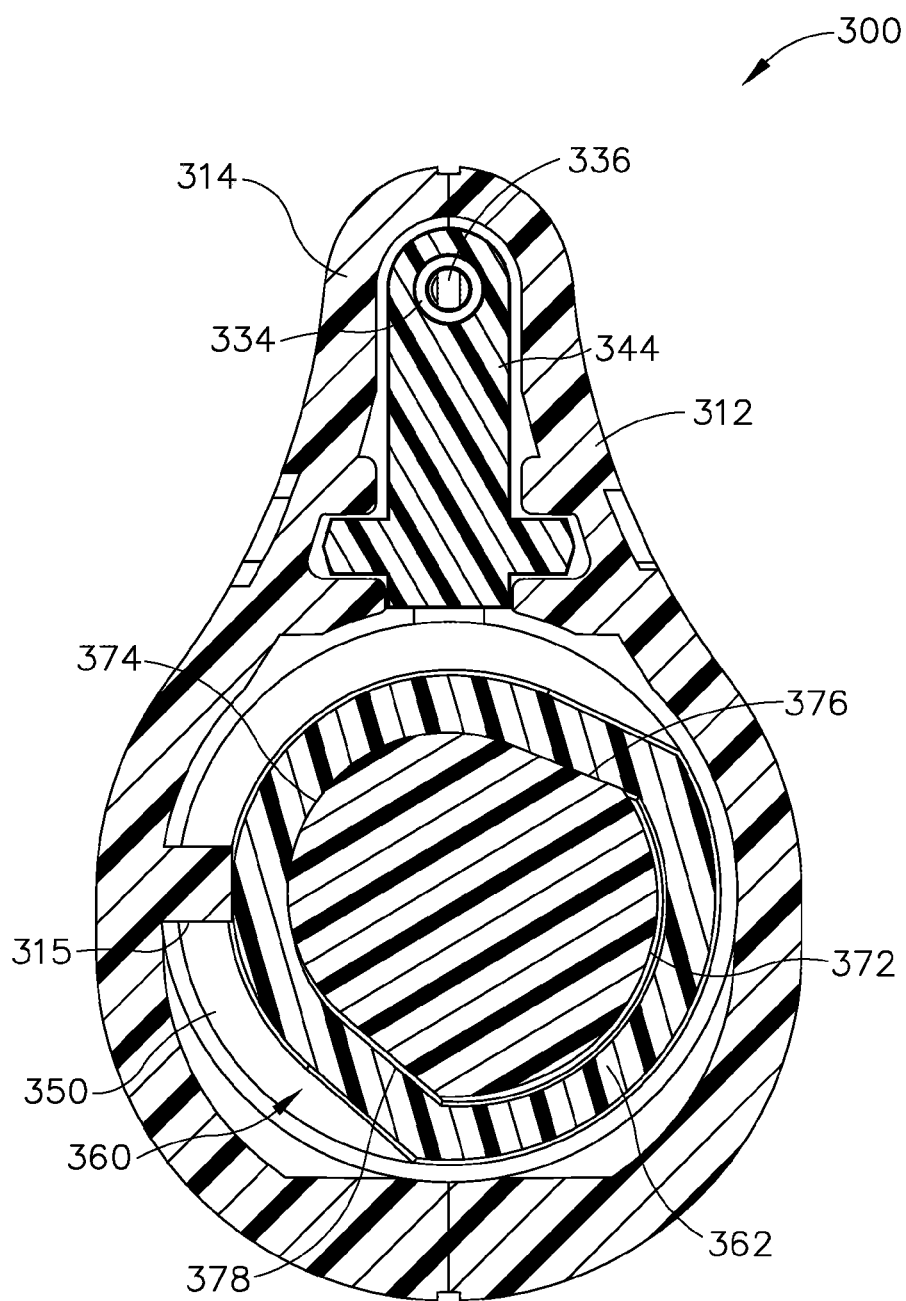
FIG. 28B depicts a cross-sectional end view of the PETDD of FIG. 21, taken along line 28-28 of FIG. 22, with the camshaft of FIG. 25 in an intermediate angular position.
Figure 28C:
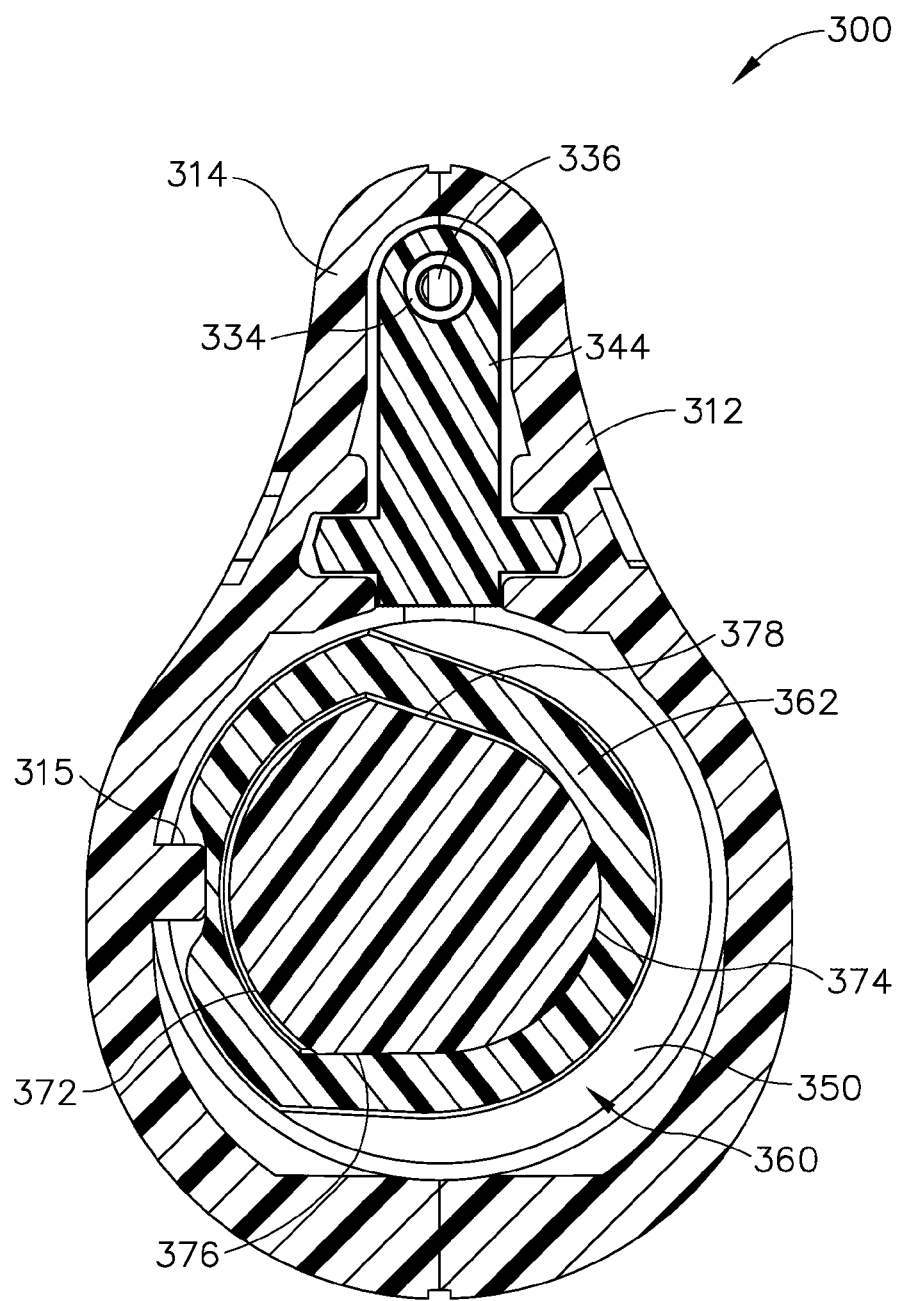
FIG. 28C depicts a cross-sectional end view of the PETDD of FIG. 21, taken along line 28-28 of FIG. 22, with the camshaft of FIG. 25 in a fired angular position.

The components of PETDD (300) described thus far are substantially identical in configuration and operation to the components of PETDD (100). One feature of PETDD (300) that differs from PETDD (100) is a braking recess (360) formed in camshaft (350). As best seen in FIGS. 27-28C, braking recess (360) is defined by a first curved surface (372), a second curved surface (374), and a pair of flat surfaces (376, 378). The outer surface of camshaft (350) has a curvature defined by a radius (r1). First curved surface (372) has a curvature defined by a radius (r2), which is smaller than radius (r1). Second curved surface (374) has a curvature defined by a radius (r3), which is smaller than radius (r2). Flat surfaces (376, 378) provide continuous transitions between curved surfaces (372, 374). In the present example, flat surfaces (376, 378) are equal in length. In some other versions, flat surfaces (376, 378) are different lengths.

As seen in FIGS. 22-28E, an o-ring (362) is positioned in braking recess (360). O-ring (362) is configured such that o-ring (362) is resiliently biased to have an inner radius (r4) that is smaller than radius (r3). O-ring (362) thus fits snugly against surfaces (372, 374, 376, 378) of braking recess (360). The exterior of o-ring (362) presents a shape or profile that is substantially identical to the shape or profile defined by surfaces (372, 374, 376, 378). In some versions, o-ring (362) is bonded to camshaft (350) by an adhesive. In some other versions, friction alone will substantially maintain the angular positioning of o-ring (362) about camshaft (350) during operation of PETDD (300).

It should be understood that curved surfaces (372, 374) may have various configurations. In the present example, the arc of curved surface (372) extends along an angular range of approximately 125 degrees; while the arc of curved surface (374) extends along an angular range of approximately 145 degrees. Of course, the arc of each curved surface (372, 374) may instead extend along any other suitable angular range. The foregoing values should therefore not be viewed as being limiting in any way.

Also in the present example, curved surfaces (372, 374) extend along arcs defined by respective radii (r2, r3) extending from the same origin—namely, an origin positioned at the central longitudinal axis of camshaft (350). In some other versions, the arcs of curved surfaces (373, 374) are defined by radii (r2, r3) extending from different origins. For instance, in some versions curved surface (372) extends along an arc defined by radius (r2) extending from an origin positioned at the central longitudinal axis of camshaft (350); while curved surface (374) extends along an arc defined by radius (r2) extending from an origin that is offset from the central longitudinal axis of camshaft (350). As yet another merely illustrative example, curved surface (372) may extend along an arc defined by radius (r2) extending from an origin that is offset from the central longitudinal axis of camshaft (350); while curved surface (374) extends along an arc defined by radius (r2) extending from an origin positioned at the central longitudinal axis of camshaft (350). As still another merely illustrative curved surface (372) may extend along an arc defined by radius (r2) extending from an origin that is offset from the central longitudinal axis of camshaft (350); while curved surface (374) extends along an arc defined by radius (r2) extending from an origin that is also offset from the central longitudinal axis of camshaft (350). It should be understood from the foregoing that, while surfaces (372, 374, 376, 378) provide symmetry about a plane that extends along and perpendicular to the longitudinal axis of camshaft (350), some other versions may lack such symmetry.

Figure 24:
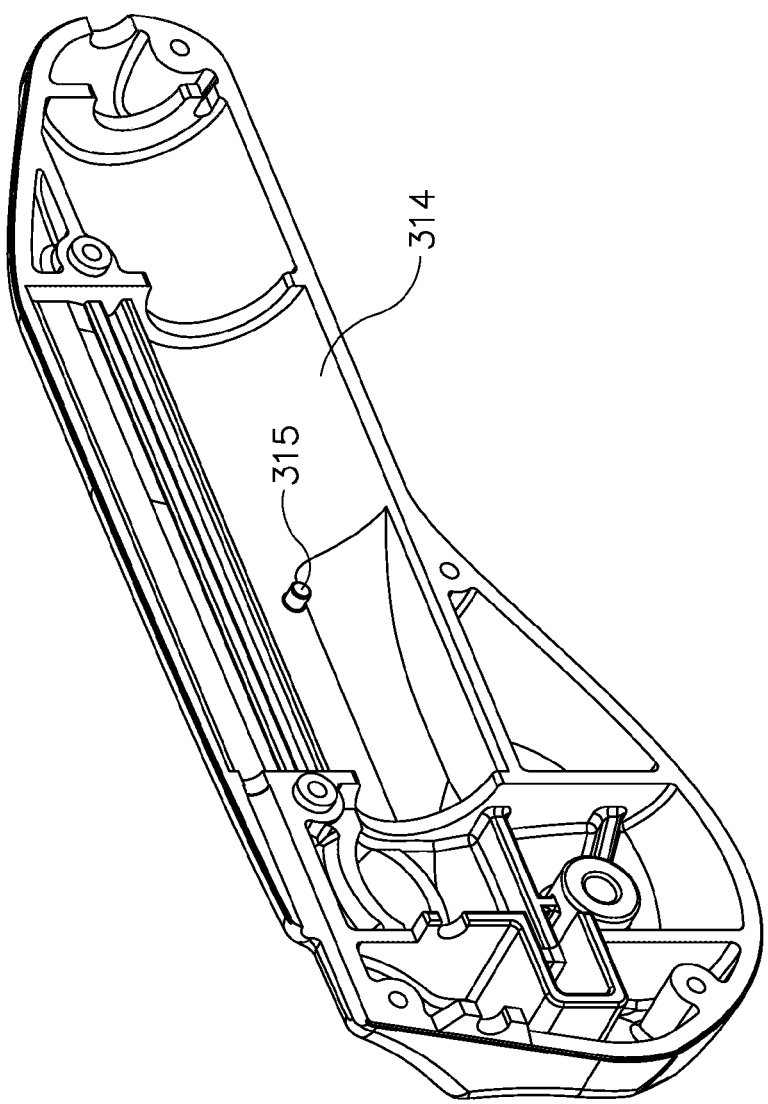
FIG. 24 depicts a perspective view of a housing half of the PETDD of FIG. 21.
Figure 25:
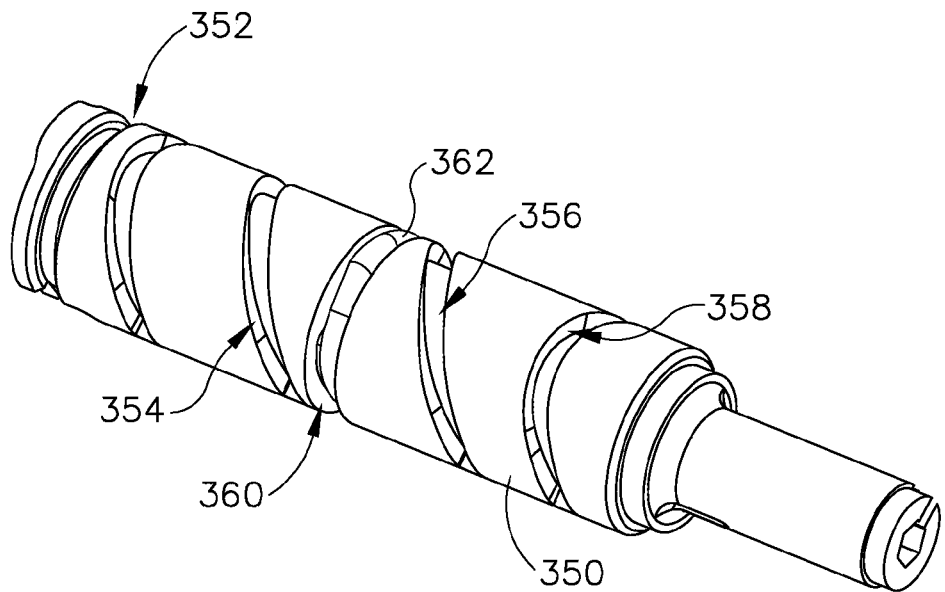
FIG. 25 depicts a perspective view of the camshaft of the PETDD of FIG. 21.
Figure 26:
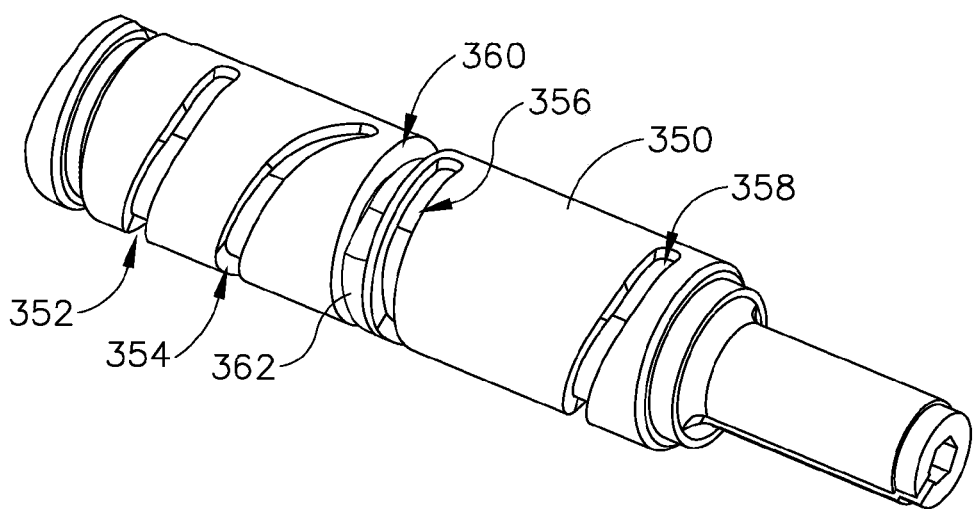
FIG. 26 depicts another perspective view of the camshaft of FIG. 25.

As shown in FIGS. 23-24, housing half (314) includes an inwardly extending boss (315). Boss (315) has a cylindraceous configuration in this example, though it should be understood that boss (315) may have any other suitable configuration. Boss (315) is positioned and configured to engage o-ring (362). In particular, FIG. 28A shows boss (315) engaging o-ring (362) when camshaft (350) is in a cocked position. In this position, the movable components of shaft assembly (320) are positioned proximally in cannula (322), a PE tube (not shown) is loaded in shaft assembly (320), torsion spring (319) is in tension, and pawl member (317) engages camshaft (350) to hold torsion spring (319) in tension. At this stage, boss (315) is engaged with o-ring (362) such that boss (315) slightly deforms o-ring (362). In particular, boss (315) engages o-ring (362) at an angular position corresponding to the location of flat surface (376). Boss (315) bears into o-ring (362) in a generally radially inward direction.

When the operator has suitably positioned tip member (324) against a patient's tympanic membrane (TM) after pulling out pull-pin (318) from handpiece (310), the operator presses pushbutton (316) laterally to allow pawl member (317) to release camshaft (350). Upon being released by pawl member (317), camshaft (350) begins to rotate about the longitudinal axis of camshaft (350), under the resilient urging of torsion spring (319). This causes linear movement of the internal components of shaft assembly (320) as described above. FIG. 28B shows PETDD (300) at an intermediate stage during this rotation of camshaft (350), with camshaft (350) having rotated clockwise from the position shown in FIG. 28A. At this stage, boss (315) has traversed the portion of o-ring (362) at an angular position corresponding to the location of second curved surface (374) and is approaching the portion of o-ring (362) at an angular position corresponding to the location of flat surface (378). Boss (315) continues to bear into o-ring (362) in a generally radially inward direction. This slight interference fit between boss (315) and o-ring (362), such that boss (315) pinches o-ring (362) against camshaft (350), provides smooth, metered rotation of camshaft (350) from the position shown in FIG. 28A to the position shown in FIG. 28B.

FIG. 28C shows PETDD (300) have camshaft (350) has completed a full actuation stroke. In this example, camshaft (350) has rotated through an angular range of approximately 270 degrees to complete a full actuation stroke, though it should be understood that some other versions may provide full actuation upon camshaft (350) rotating through any other suitable angular range. At this stage, the internal components of shaft assembly (320) have completed the linear movement sequence described above to deploy a PE tube (200) in the patient's tympanic membrane (TM). In reaching this stage, boss (315) has traversed the portion of o-ring (362) at an angular position corresponding to the location of flat surface (378); and part of the portion of o-ring (362) at an angular position corresponding to the location of first curved surface (372). Friction between boss (315) and o-ring (362) has brought camshaft (350) to a halt.

Since the radius (r2) is larger than the radius (r3), boss (315) bears into o-ring (362) to a greater extent at the stage shown in FIG. 28C than in previous stages of the actuation sequence. Boss (315) thus bears into o-ring (362) in a generally radially inward direction to such an extent that o-ring (362) is more deformed (elastically) at this stage than at previous stages of the actuation sequence. It should be understood that the degree of pinching or interference between boss (315) and o-ring (362) gradually increases during the time between the stage shown in FIG. 28B and the stage shown in FIG. 28C. This gradually increasing pinching or interference provides a gradual braking effect or deceleration. This deceleration is more gradual than the deceleration provided by elastomeric plug (135) of PETDD (100). By providing a more gradual deceleration, PETDD (300) of this example may transmit less vibration to the patient's tympanic membrane (TM) via shaft assembly (320) than would otherwise be transmitted to the patient's tympanic membrane (TM) via shaft assembly (115) of PETDD (100). In addition or in the alternative, the combination of o-ring (362) and boss (315) may make actuation of PETDD (300) less audible to the patient than the actuation of PETDD (100) otherwise would be.

In some instances, PETDD (300) with braking recess (360) and o-ring (362) may provide a peak braking sound of approximately 70 dB; while a PETDD (100) that lacks braking recess (360) and o-ring (362) may provide a peak braking sound of approximately 110 dB. Alternatively, PETDD (300) may provide any other degree of reduction in the braking sound. It should also be understood that PETDD (300) may include dampening grease in braking recess (360) in order to provide further dampening.

In the present example, as soon as camshaft (350) is actuated, camshaft (350) completes an actuation rotation stroke in less than approximately 500 ms. In other words, as soon as the operator has pressed pushbutton (316) to a sufficient degree that torsion spring (319) drives camshaft (350) to rotate, such rotation occurs for less than approximately 500 ms before boss (315) and o-ring (362) bring camshaft (350) to a halt. The actuation stroke for PETDD (300) may thus be completed within less than approximately 500 ms. Alternatively, camshaft (350) may rotate for any other suitable duration to complete an actuation stroke.

O-ring (362) and braking recess (360) of the present example are both positioned along a plane that is perpendicular to the longitudinal axis of camshaft (350). In some other versions, o-ring (362) and braking recess (360) are positioned along a plane that is obliquely angled relative to the longitudinal axis of camshaft (350). In some such versions, boss (315) engages a proximal face or a distal face of o-ring (362), such that boss (315) drives further into the proximal face or a distal face of o-ring (362) as camshaft rotates (350); rather than boss (315) driving further radially inwardly into o-ring (362) as camshaft rotates (350) as illustrated in FIGS. 28A-28C.

In the present example, boss (315) is substantially rigid. By way of example only, boss (315) may comprise rigid plastic that is molded as a unitary feature of housing half (314). In some other versions, boss (315) comprises a metallic pin that is fixedly secured in housing half (314). Other suitable ways in which rigid versions of boss (315) may be formed will be apparent to those of ordinary skill in the art in view of the teachings herein. As another merely illustrative alternative, boss (315) may comprise an elastomeric material. By way of example only, boss (315) may include an elastomeric cap or overmold that is positioned about a rigid post, peg, or pin. Alternatively, boss (315) may be formed of an elastomeric material, such that boss (315) is not internally rigid. Other suitable ways in which boss (315) may be formed of elastomeric material or otherwise incorporate elastomeric material will be apparent to those of ordinary skill in the art in view of the teachings herein. It should also be understood that, in versions where boss (315) is formed of elastomeric material or otherwise incorporates elastomeric material, camshaft (350) may still include o-ring (362). The elastomeric material of boss (315) may thus directly engage o-ring (362) in a manner similar to that shown in FIGS. 28A-28C. Alternatively, o-ring (362) may be omitted. For instance, the elastomeric material of boss (315) may directly engage surfaces (372, 374, 376, 378) during the sequence shown in FIGS. 28A-28C.

As yet another merely illustrative alternative, boss (315) may be spring-loaded in housing half (314), such that boss (315) is resiliently biased to bear against o-ring (362) or surfaces (372, 374, 376, 378) during the sequence shown in FIGS. 28A-28C. For instance, a coil spring, leaf spring, or other resilient member(s) may be interposed between boss (315) and housing half (314) to provide such a resilient bias to boss (315). In versions where boss (315) is resiliently biased toward o-ring (362) and camshaft (350), boss (315) may be rigid as described above, may incorporate an elastomeric material, may be formed of an elastomeric material, or may have any other suitable properties. Furthermore, in versions where boss (315) is resiliently biased toward o-ring (362) and camshaft (350), boss (315) may directly contact o-ring as described above. Alternatively, o-ring may be omitted and boss (315) may directly contact surfaces (372, 374, 376, 378) during the sequence shown in FIGS. 28A-28C.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In some instances, the device is sterilized using conventional ethylene oxide sterilization techniques and systems. In some other instances, the device is placed in a closed and sealed container, such as a plastic or TYVEK bag; and the container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, steam, etc.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument, comprising:
   a handpiece;
   a boss member fixed relative to the handpiece;
   a cam body rotatably supported within the handpiece and including a cam profile;
   a shaft assembly;
   a cam follower coupled to a portion of the shaft assembly and movably engaged with the cam profile of the cam body such that the cam profile and the cam follower are configured to cooperatively drive movement of the shaft assembly in response to a rotation of the cam body; and
   a braking member extending along a portion of the cam body such that the boss member contacts the braking member when the cam body is in a cocked position, and wherein the braking member can progressively engage the boss member as the cam body rotates to brake the rotation of the cam body.

2. The instrument of claim 1, wherein the braking member is formed of an elastomeric material.

3. The instrument of claim 1, wherein the braking member includes an O-ring.

4. The instrument of claim 1, wherein the cam body defines a recess in which at least a portion of the braking member is disposed.

5. An instrument comprising:
   a handpiece;
   a boss member fixed relative to the handpiece;
   a cam body rotatably supported within the handpiece and including a cam profile and a recess;
   a shaft assembly;
   a cam follower coupled to a portion of the shaft assembly and movably engaged with the cam profile of the cam body such that the cam profile and the cam follower are configured to cooperatively drive movement of the shaft assembly in response to a rotation of the cam body; and
   a braking member, at least a portion of the braking member is disposed in the recess of the cam body, the braking member extending along a portion of the cam body such that the braking member can progressively engage the boss member as the cam body rotates to brake the rotation of the cam body;
   wherein the recess is defined in part by a first curved surface and a second curved surface, the first curved surface having a first curvature defined by a first radius and the second curved surface having a second curvature defined by a second radius different from the first radius.

6. The instrument of claim 5, wherein the recess is further defined by a flat surface extending from a first end of the first curved surface to a first end of the second curved surface.

7. The instrument of claim 6, wherein the flat surface is a first flat surface, the recess further defined by a second flat surface extending from a second end of the first curved surface to a second end of the second curved surface.

8. The instrument of claim 5, wherein the first curved surface and the second curved surface extend along a common plane.

9. The instrument of claim 8, wherein the cam body is a camshaft that extends along a longitudinal axis, and the common plane is perpendicular to the longitudinal axis.

10. The instrument of claim 1, wherein the handpiece includes a housing that is unitarily formed with the boss member.

11. The instrument of claim 1, wherein the boss member is rigid.

12. The instrument of claim 1, wherein the boss member is configured to bear inwardly on the braking member.

13. The instrument of claim 1, further comprising a torsion spring configured to rotate the cam body.

14. An instrument, comprising:
a handpiece;
a boss member fixed relative to the handpiece;
a cam body rotatably supported within the handpiece and including a cam profile;
a shaft assembly;
a cam follower coupled to a portion of the shaft assembly and movably engaged with the cam profile of the cam body such that the cam profile and the cam follower are configured to cooperatively drive movement of the shaft assembly in response to a rotation of the cam body; and
a braking member extending along a portion of the cam body such that the braking member can progressively engage the boss member as the cam body rotates to brake the rotation of the cam body;
wherein the boss member is resiliently biased to bear against the braking member.

15. An instrument, comprising:
a handpiece;
a boss member fixed relative to the handpiece;
a cam body rotatably supported within the handpiece and including a cam profile;
a shaft assembly;
a cam follower coupled to a portion of the shaft assembly and movably engaged with the cam profile of the cam body such that the cam profile and the cam follower are configured to cooperatively drive movement of the shaft assembly in response to a rotation of the cam body; and
a braking member extending along a portion of the cam body such that the braking member can progressively engage the boss member as the cam body rotates to brake the rotation of the earn body;
a spring configured to bias the boss member such that the boss member engages the braking member.

16. The instrument of claim 1, wherein the shaft assembly is operable to deploy a pressure equalization tube in a tympanic membrane in response to the rotation of the cam body.

17. An instrument, comprising:
a handpiece;
a boss member fixed relative to the handpiece;
a cam body rotatably supported within the handpiece and extending along a longitudinal axis;
a shaft assembly extending from the handpiece and operable to pierce a tympanic membrane in response to a rotation of the cam body; and
an elastomeric member extending along a first portion of the cam body and along a second portion of the cam body, the first portion of the cam body located a first distance from the longitudinal axis of the cam body and the second portion of the cam body located a second distance from the longitudinal axis of the cam body and different from the first distance, the elastomeric member configured to progressively engage the boss member as the cam body rotates to brake the rotation of the cam body, and
wherein the elastomeric member is an O-ring.

18. An instrument, comprising:
a housing defining an interior space;
a shaft assembly moveable to pierce a tympanic membrane;
a cam body disposed within the interior space and configured to rotate to drive movement of the shaft assembly, the cam body including a portion having a plurality of surfaces; and
a boss extending inwardly from the housing and configured to engage at least one of the plurality of surfaces to brake a rotation of the cam body;
wherein the plurality of surfaces includes a first curved surface disposed a first distance from an inner surface of the housing and a second curved surface disposed a second distance from the inner surface of the housing and different from the first distance, such that the boss is configured to gradually brake the rotation of the cam body.

* * * * *